(12) United States Patent
Tamamura et al.

(10) Patent No.: US 8,445,291 B2
(45) Date of Patent: May 21, 2013

(54) METHOD FOR DETECTING TARGET SUBSTANCE, AND TAG, DNA, VECTOR, PROBE AND DETECTION KIT FOR USE THEREWITH

(75) Inventors: Hirokazu Tamamura, Tokyo (JP); Hiroshi Tsutsumi, Tokyo (JP)

(73) Assignee: National University Corporation Tokyo Medical and Dental University, Tokyo (JP)

( * ) Notice: Subject to any disclaimer, the term of this patent is extended or adjusted under 35 U.S.C. 154(b) by 501 days.

(21) Appl. No.: 12/586,425

(22) Filed: Sep. 22, 2009

(65) Prior Publication Data

US 2010/0075434 A1    Mar. 25, 2010

Related U.S. Application Data

(63) Continuation of application No. PCT/JP2008/055399, filed on Mar. 24, 2008.

(30) Foreign Application Priority Data

Mar. 23, 2007    (JP) ................................ 2007-077916

(51) Int. Cl.
  *G01N 21/76*    (2006.01)

(52) U.S. Cl.
  USPC .................. 436/172; 436/56; 560/13; 560/44

(58) Field of Classification Search
  None
  See application file for complete search history.

(56) References Cited

PUBLICATIONS

Engfeldt, Torun, et al. Chemical synthesis of triple-labelled three-helix bundle binding proteins for speicific fluorescent detection of unlabelled protein, 2005, ChemBioChem, vol. 6, pp. 1043-1050.*
Cao, Haishi, et al. CrAsH: abiarsenical multi-use affinity probe with low non-psecific fluorescence, 2006, Chem. Communication, pp. 2601-2603.*
Tripet, Brian, et al. Engineering a de novo-designed coiled-coil heterodimerization domain for the rapid detection, purification and characterization of recombinantly expressed peptides and proteins, 1996, Protein Engineering, vol. 9(11),pp. 1029-1042.*
Chen, I, et al., "Site-Specific Labeling of Proteins with Small Molecules in Live Cells," Current Opinion in Biotechnology, vol. 16, pp. 35-40 (2005).
Ojida, A., et al., "Oligo-Asp Tag/An(II) Complex Probe as a New Pair for Labeling and Fluorescence Imaging of Proteins," J. Am. Chem. Soc., vol. 128, pp. 10452-10459 (2006).
Obataya, I., et al., "Design and Synthesis of 3α-Helix Peptides Forming a Cavity for a Fluorescent Ligand," Biopolymers, vol. 59, pp. 65-71 (2001).

* cited by examiner

*Primary Examiner* — Robert Xu
(74) *Attorney, Agent, or Firm* — Carmody & Torrance LLP

(57) ABSTRACT

Provide is a method for detecting a target substance, which method can visualize the expression of the target substance at any time point while reducing influences on the functions of the target substance, can use fluorescent dyes having various excitation/emission wavelengths, and can achieve easy staining process. Also provided are a tag, a DNA, a vector, a probe and a detection kit suitable for use in the above-described detection method. Specifically, the method for detecting a target substance, comprises the steps of bringing into contact with each other (a) a tag comprising a polypeptide forming an α-helix structure, the tag bound to the target substance, and (b) a probe comprising a compound bound to a fluorescent dye; and measuring the fluorescence emitted by the fluorescent dye. The binding of the tag α-helix structure to the probe compound induces a spectral change in the fluorescence emitted by the fluorescent dye.

7 Claims, 14 Drawing Sheets

FIG. 3A
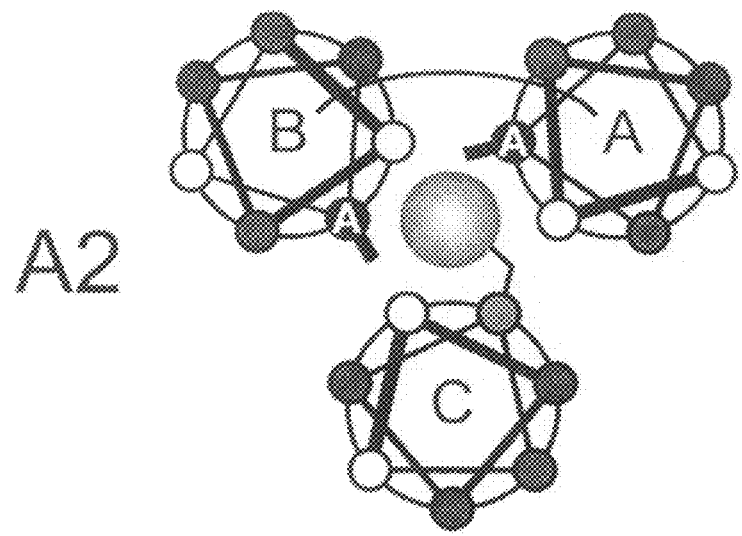
A2
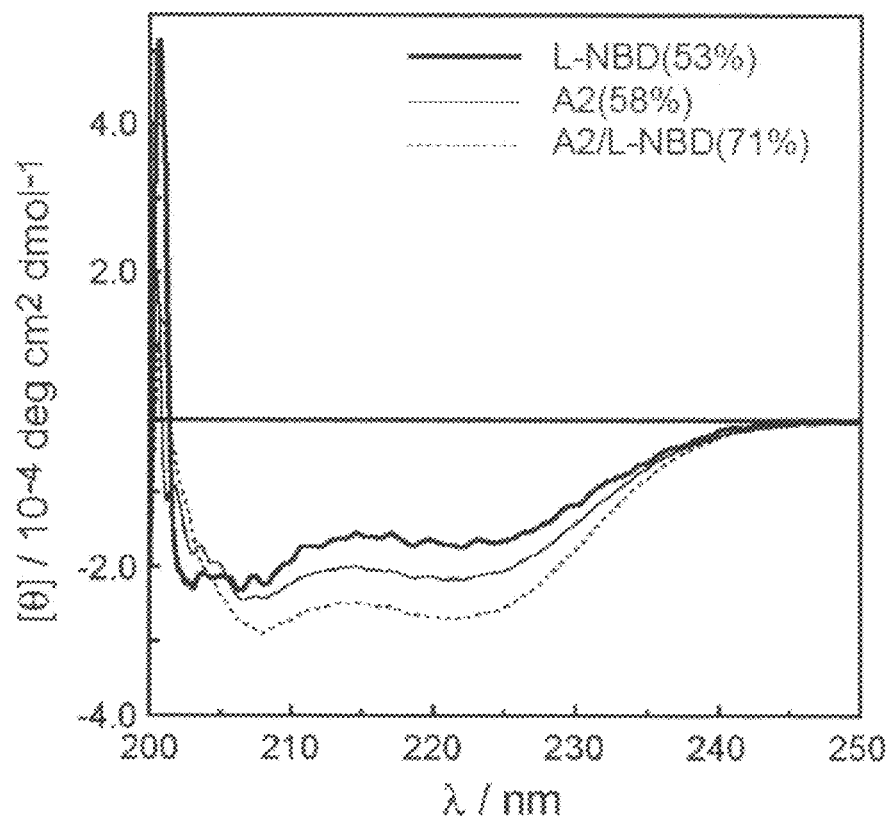
[L-NBD] = 1.0 μM
[A2] = 1.0 μM
[L-NBD] = [A2] = 1.0 μM
in 50 mM Tris HCl buffer (pH 7.2, 100 mM NaCl)

[L-NBD] = 1.0 μM
[L2] = 1.0 μM
[L-NBD] = [L2] = 1.0 μM
in 50 mM Tris HCl buffer (pH 7.2, 100 mM NaCl)

[L-NBD] = 1.0 μM
[G2] = 1.0 μM
[L-NBD] = [G2] = 1.0 μM
in 50 mM Tris HCl buffer (pH 7.2, 100 mM NaCl)

FIG. 4A
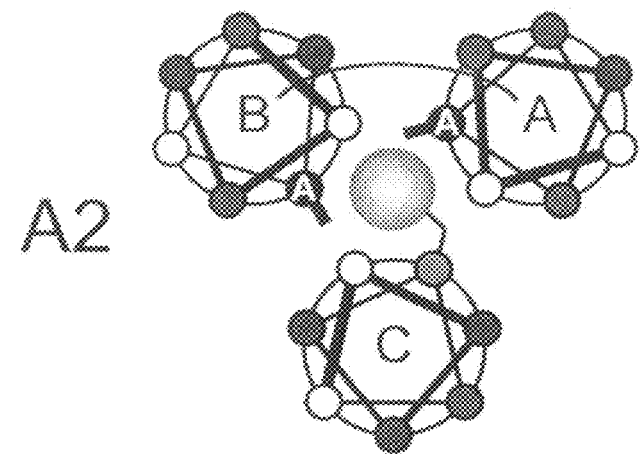
A2
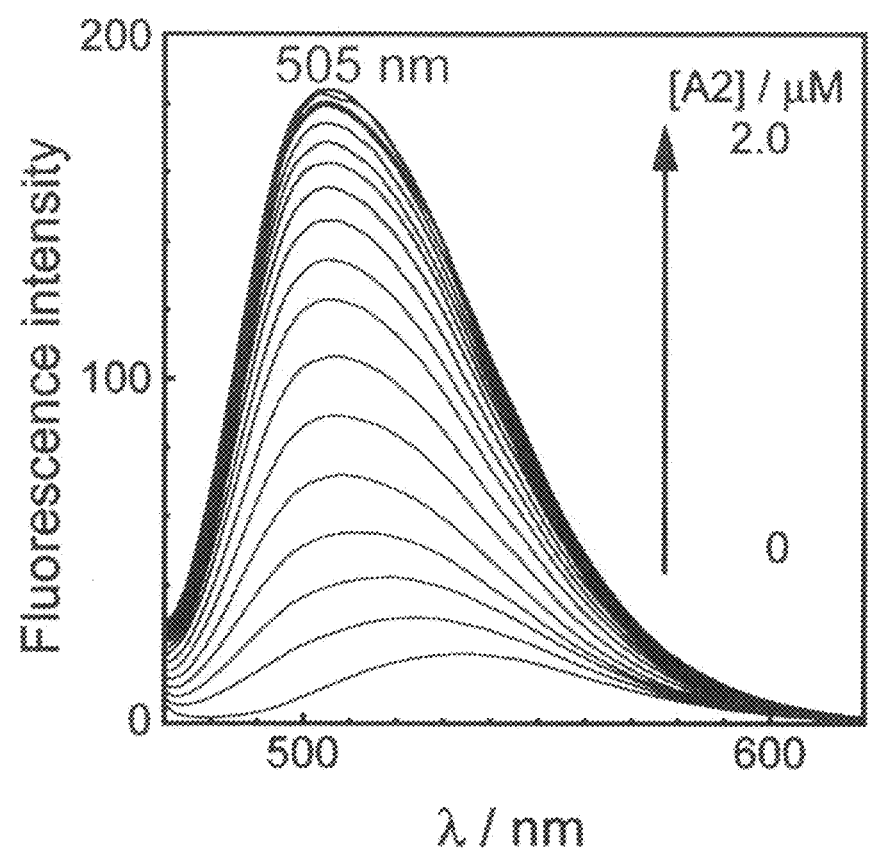

FIG. 4C
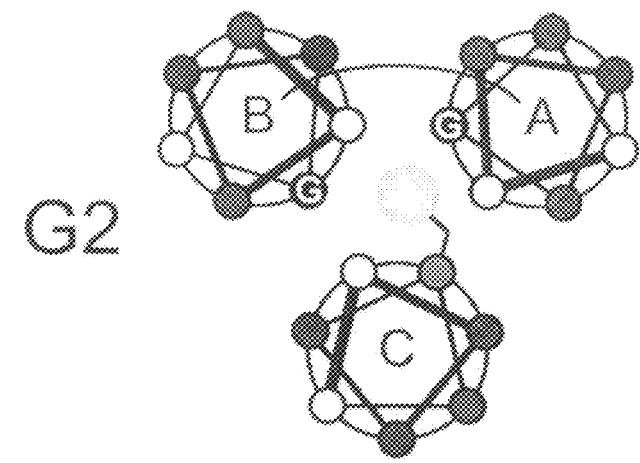
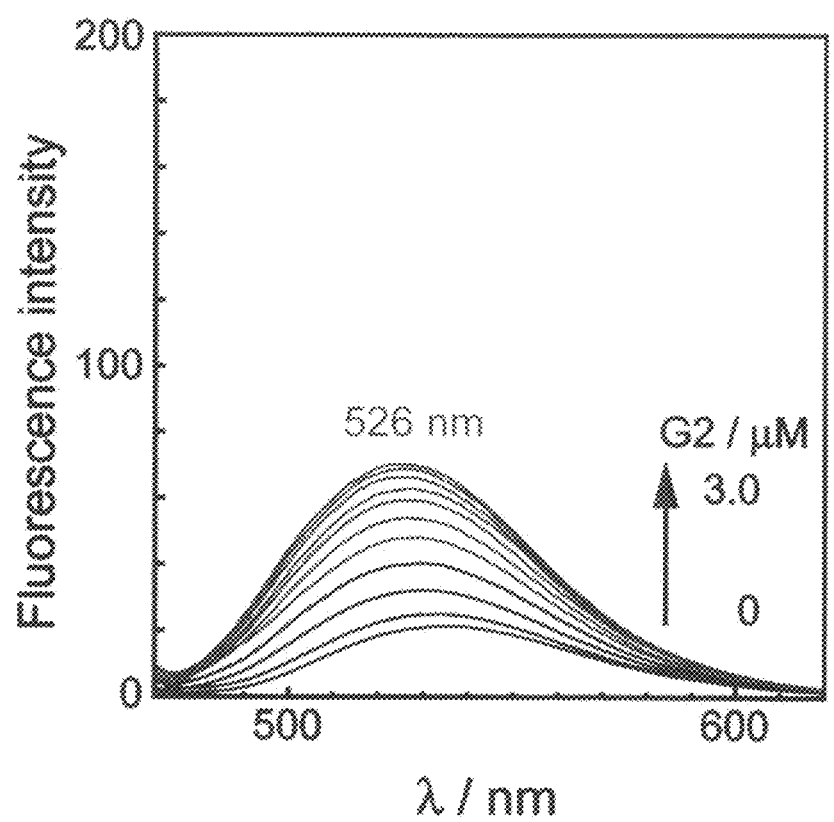

C1: Tag concentration
C2: Probe concentration

[L-NBD] = 0.5 μM
in 50 mM HEPES buffer (pH 7.2, 100 mM NaCl)
λex = 456 nm

SEQUENCE LISTING

```
<160> NUMBER OF SEQ ID NOS: 5

<210> SEQ ID NO 1
<211> LENGTH: 47
<212> TYPE: PRT
<213> ORGANISM: Artificial Sequence
<220> FEATURE:
<223> OTHER INFORMATION: Designed tag polypeptide to form alpha helix

<400> SEQUENCE: 1

Ala Leu Lys Lys Glu Leu Glu Ala Ala Lys Lys Glu Leu Glu Ala Leu
1               5                   10                  15

Lys Lys Glu Leu Ala Gly Gly Cys Gly Gly Ala Leu Glu Lys Glu Leu
            20                  25                  30

Glu Ala Leu Glu Lys Glu Ala Glu Ala Leu Glu Lys Glu Leu Ala
        35                  40                  45

<210> SEQ ID NO 2
<211> LENGTH: 21
<212> TYPE: PRT
<213> ORGANISM: Artificial Sequence
<220> FEATURE:
<223> OTHER INFORMATION: Designed probe polypeptide to form alpha helix
<220> FEATURE:
<221> NAME/KEY: MISC_FEATURE
<222> LOCATION: (13)..(13)
<223> OTHER INFORMATION: Xaa stands for 2,3-Diaminopropionic acid
      conjugated NBD

<400> SEQUENCE: 2

Ala Leu Lys Lys Lys Leu Glu Ala Leu Lys Lys Lys Xaa Glu Ala Leu
1               5                   10                  15

Lys Lys Lys Leu Ala
            20
```

<210> SEQ ID NO 3
<211> LENGTH: 47
<212> TYPE: PRT
<213> ORGANISM: Artificial Sequence
<220> FEATURE:
<223> OTHER INFORMATION: Designed tag polypeptide to form alpha helix

<400> SEQUENCE: 3

```
Ala Leu Lys Lys Glu Leu Glu Ala Leu Lys Lys Glu Leu Glu Ala Leu
1               5                   10                  15

Lys Lys Glu Leu Ala Gly Gly Cys Gly Gly Ala Leu Glu Lys Glu Leu
            20                  25                  30

Glu Ala Leu Glu Lys Glu Leu Glu Ala Leu Glu Lys Glu Leu Ala
        35                  40                  45
```

<210> SEQ ID NO 4
<211> LENGTH: 47
<212> TYPE: PRT
<213> ORGANISM: Artificial Sequence
<220> FEATURE:
<223> OTHER INFORMATION: Designed tag polypeptide to form alpha helix

<400> SEQUENCE: 4

```
Ala Leu Lys Lys Glu Leu Glu Ala Gly Lys Lys Glu Leu Glu Ala Leu
1               5                   10                  15

Lys Lys Glu Leu Ala Gly Gly Cys Gly Gly Ala Leu Glu Lys Glu Leu
            20                  25                  30

Glu Ala Leu Glu Lys Glu Gly Glu Ala Leu Glu Lys Glu Leu Ala
        35                  40                  45
```

<210> SEQ ID NO 5
<211> LENGTH: 22
<212> TYPE: PRT
<213> ORGANISM: Artificial Sequence
<220> FEATURE:
<223> OTHER INFORMATION: Designed probe polypeptide to form alpha helix
<220> FEATURE:
<221> NAME/KEY: MISC_FEATURE
<222> LOCATION: (1)..(1)
<223> OTHER INFORMATION: Xaa stands for chloroacetylated glycine
<220> FEATURE:
<221> NAME/KEY: MISC_FEATURE
<222> LOCATION: (14)..(14)
<223> OTHER INFORMATION: Xaa stands for 2,3-Diaminopropionic acid
      conjugated NBD

<400> SEQUENCE: 5

```
Xaa Ala Leu Lys Lys Lys Leu Glu Ala Leu Lys Lys Lys Xaa Glu Ala
1               5                   10                  15

Leu Lys Lys Lys Leu Ala
            20
```

METHOD FOR DETECTING TARGET SUBSTANCE, AND TAG, DNA, VECTOR, PROBE AND DETECTION KIT FOR USE THEREWITH

CROSS-REFERENCE TO RELATED APPLICATION

This is a continuation application of PCT/JP2008/055399, filed on Mar. 24, 2008. This application is based upon and claims the benefit of priority of the prior Japanese Patent Application No. 2007-077916, filed on Mar. 23, 2007, and the International Application No. PCT/JP2008/055399, filed on Mar. 24, 2008, the entire contents of which are incorporated herein by reference.

This application incorporates by reference the material contained on the compact disc submitted herewith. The disc contains the file entitled Sequence Listing (text format) N-MD001-08P-US.txt, which was created on Sep. 16, 2009.

BACKGROUND OF THE INVENTION

1. Field of the Invention

The present invention relates to a method for detecting target substances, as well as to tags, DNA, vectors, probes and detection kits for use with such a method. In particular, the present invention relates to a method for detecting target substances using a polypeptide tag forming an α-helix structure, as well as to tags, DNA, vectors, probes and detection kits for use with such a method.

2. Description of the Related Art

Bioimaging, a technique for visualizing a target protein of interest by selectively labeling it with a fluorescent label, is commonly used for real-time monitoring of expression dynamics and functions of proteins (or polypeptides) within or outside cells. Among widely used techniques for bioimaging of proteins are immunostaining with antibodies labeled with various fluorescent dyes (fluorescent-labeled antibodies) and fusion of target-proteins with fluorescent proteins.

One drawback of immunostaining is that the technique requires as many different fluorescent-labeled antibodies as target proteins and such antibodies are expensive and readily lose their activity. Another disadvantage of immunostaining is that it is difficult to distinguish fluorescent-labeled antibodies bound to target proteins from unbound fluorescent-labeled antibodies, which must be washed off to allow the detection of the target proteins, requiring additional labor.

Concerning the fusion with fluorescent proteins, fluorescent proteins can be incorporated into target proteins as desired using techniques commonly used in the field of genetic engineering. Nonetheless, the wavelength range of excitation/emission that can be used in the detection of fluorescence tends to be limited depending on the type of the fused fluorescent protein.

Another disadvantage of fusion technique is that once a fluorescent protein is expressed, it remains visualized until it is decomposed, so that the timing for visualization cannot be selected as desired. Furthermore, many fluorescent proteins used in the fusion technique are relatively large in size and often affect structure and functions of target proteins.

A new technique for fluorescent labeling of target proteins has recently been proposed. In this technique, a peptide tag is fused with a target protein and the tagged target protein is fluorescent-labeled with tag-specific fluorescent probe molecules (The technique is referred to as "labeling method," hereinafter). Much effort has been devoted to developing suitable tag/probe pairs for use in the labeling method (See, for example, C. Irwin, et al., Curr. Opin. Biotechnol., 2005, 16, 35-40; and A. Ojida, et al., J. Am. Chem. Soc., 2006, 128, 10452-10459). The labeling method enables the use of a variety of fluorescent molecules obtained by organic synthesis. In addition, the method, in which tag-fused proteins are expressed prior to labeling, allows detection of target proteins at any time point and at various excitation/emission wavelengths. However, it is considered difficult to distinguish fluorescent probe molecules bound to the tag-fused proteins from the unbound fluorescent probe molecules, which must be washed off to allow the detection of the target proteins, requiring additional labor.

Leucine zipper is one of the known higher structures of peptide chains found in proteins. It is a higher structure formed by two or more α-helices of peptides that are highly complementary to and, thus, have high affinity for one another. The α-helices are held together through hydrophobic interaction and electrostatic interaction. An α-helix structure is a right-handed helix of amino acids that has 3.6 amino acids in each turn with a pitch of 0.54 nm. Each carbonyl group in the polypeptide chain forms a hydrogen bond with the amide of the amino acid four residues ahead in the polypeptide chain, forming a substantially linear backbone that makes the structure highly stable.

Recent studies report that hydrophobic pockets can be formed within a peptide bundle having a leucine zipper structure consisting of three α-helices by replacing hydrophobic amino acids in the peptide bundle with amino acids having small side chains. Fluorescent dyes and other small organic molecules can be incorporated into such pockets (See, for example, I. Obataya, et al., Biopolymers, 2001, 59, 65-71).

BRIEF SUMMARY OF THE INVENTION

The present invention addresses the above-described problems of prior art by achieving the following objectives. Accordingly, it is an objective of the present invention to provide a method for detecting a target substance, which method can visualize the expression of the target substance at any time point while reducing influences on the functions of the target substance, can use fluorescent dyes having various excitation/emission wavelengths, and can achieve easy staining process. It is another objective of the present invention to provide a tag, a DNA, a vector, a probe and a detection kit suitable for use in the above-described detection method.

In the course of studies to find a way to solve the above-described problems, the present inventors have made the following findings. Specifically, the present inventors have found that when a particular fluorescent dye whose fluorescence spectrum can shift in a hydrophobic environment is incorporated into a hydrophobic pocket that has been formed within a peptide bundle consisting of three α-helices that form a leucine zipper structure, the fluorescence spectrum of the fluorescent dye will shift.

As described above, studies report that hydrophobic pockets can be formed within a three α-helix peptide bundle having a leucine zipper structure by replacing hydrophobic amino acids in the peptide bundle with amino acids having small side chains, and that fluorescent dyes and other small organic molecules can be incorporated into such pockets.

We have found that certain fluorescent dyes whose emission wavelength shifts and fluorescence increases in response to environmental changes from hydrophilic to hydrophobic conditions can be induced to exhibit a shift in emission wavelength and an increase in fluorescence intensity corresponding to their labeling by controlling the surrounding environment from hydrophilic to hydrophobic conditions through the formation of leucine zipper structure. This is an entirely new finding suggested by no other studies.

The present inventors have also found that by taking advantage of the pockets formed within a three α-helix peptide bundle forming a leucine zipper structure, spectral changes can be induced not only in the fluorescence of fluorescent dyes that can undergo spectral changes in hydrophobic environment, but also in the fluorescence of various other fluorescent dyes.

The present inventors have also found that by taking advantage of the pockets formed within a three α-helix peptide bundle forming a leucine zipper structure, the distance between two molecules can be controlled, which may be useful, for example, in fluorescence resonance energy transfer (FRET), control of fluorescence using quenchers, and excimer fluorescence.

The present invention is based upon the insights of the present inventors, and means for solving the problems are as follow:

<1> A method for detecting a target substance, containing: bringing into contact with each other (a) a tag containing a polypeptide forming an α-helix structure, the tag bound to the target substance, and (b) a probe containing a compound bound to a fluorescent dye; and measuring the fluorescence emitted by the fluorescent dye, wherein a binding of the α-helix structure of the tag to the compound of the probe induces a spectral change in the fluorescence emitted by the fluorescent dye.

<2> The method according to <1>, wherein the binding of the α-helix structure of the tag to the compound of the probe contains hydrophobic interaction.

<3> The method according to <2>, wherein the binding of the α-helix structure of the tag to the compound of the probe contains electrostatic interaction.

<4> The method according to any one of <1> to <3>, wherein the compound of the probe contains a polypeptide forming an α-helix structure and the fluorescent dye is bound to the α-helix structure of the probe.

<5> The method according to any one of <1> to <4>, wherein at least one α-helix structure of the tag and at least one α-helix structure of the probe are associated with each other in at least one of parallel orientation and antiparallel orientation, forming a tag-probe complex with the hydrophobic surface of each α-helix facing inward.

<6> The method according to any one of <1> to <5>, wherein the α-helix structure of the tag contains seven or more consecutive amino acid residues of an amino acid sequence represented by the following structural formula (1):

$$\{X_1-X_2-X_3-X_4-X_5-X_6-X_7\}_N \quad (1)$$

wherein N is an integer of 2 or greater; $X_3$ and $X_5$ are each an acidic amino acid or a basic amino acid; $X_2$ and $X_6$ are each a hydrophobic amino acid; and $X_1$, $X_4$ and $X_7$ are each any amino acid.

<7> The method according to <6>, wherein at least one of amino acid residues $X_2$ and $X_6$ present in at least one α-helix structure of the tag is substituted with one of glycine, alanine, valine, serine, threonine and asparagine.

<8> The method according to any one of <1> to <7>, wherein the tag contains two or more α-helix structures.

<9> The method according to <8>, wherein the α-helix structures of the tag are linked to one another via a linker peptide containing an amino acid.

<10> The method according to any one of <4> to <9>, wherein the probe α-helix structure contains seven or more consecutive amino acid residues of an amino acid sequence represented by the following structural formula (1):

$$\{X_1-X_2-X_3-X_4-X_5-X_6-X_7\}_N \quad (1)$$

wherein N is an integer of 2 or greater; $X_3$ and $X_5$ are each an acidic amino acid or a basic amino acid; $X_2$ and $X_6$ are each a hydrophobic amino acid; and $X_1$, $X_4$ and $X_7$ are each any amino acid, and at least one of amino acid residues $X_2$ and $X_6$ present in at least one α-helix structure of the probe is substituted with a molecule bound to a fluorescent dye.

<11> The method according to any one of <4> to <11>, wherein the probe contains two or more α-helix structures.

<12> The method according to <11>, wherein the α-helix structures of the tag are linked to one another via a linker peptide containing an amino acid.

<13> The method according to any of <11> or <12>, wherein when the probe contains an α-helix structure with no fluorescent dye bound thereto, at least one of amino acid residues $X_2$ and $X_6$ present in at least one α-helix structure is substituted with one of glycine, alanine, valine, serine, threonine and asparagine.

<14> The method according to <4>, wherein the polypeptide of the tag contains a sequence represented by the following structural formula (2) and the polypeptide of the probe contains a sequence represented by the following structural formula (3):

Tag: (2)

$\{X_1-\epsilon_1-\alpha-X_4-\beta-\gamma-X_7\}\ \{X_1-\epsilon_2-\alpha-X_4-\beta-\gamma-X_7\}$ $\{X_1-\epsilon_3-\alpha-X_4-\beta-\gamma-X_7\}\ \{X_M\}\ \{X_1-\gamma-\beta-X_4-\beta-\epsilon_3-X_7\}$ $\{X_1-\gamma-\beta-X_4-\beta-\epsilon_2-X_7\}\ \{X_1-\gamma-\beta-X_4-\beta-\epsilon_1-X_7\}$ Probe: (3)

$\{X_1-\gamma-\alpha-X_4-\alpha-\sigma_1-X_7\}\ \{X_1-\gamma-\alpha-X_4-\alpha-\sigma_2-X_7\}$ $\{X_1-\gamma-\alpha-X_4-\alpha-\sigma_3-X_7\}$ wherein α is an acidic amino acid or a basic amino acid; β is a basic amino acid when α is an acidic amino acid, and is an acidic amino acid when α is a basic amino acid; γ is a hydrophobic amino acid; at least one of $\sigma_1$ to $\sigma_3$ is a molecule bound to a fluorescent dye and the rest of $\sigma_1$ to $\sigma_3$ are each a hydrophobic amino acid; $\epsilon_1$ is each independently one of glycine, alanine, valine, serine, threonine and asparagine when $\sigma_2$ is the fluorescent dye-bound molecule, and is each independently a hydrophobic amino acid when $\sigma_2$ is a hydrophobic amino acid; $\epsilon_2$ is each independently one of glycine, alanine, valine, serine, threonine and asparagine when $\sigma_3$ is the fluorescent dye-bound molecule, and is each independently a hydrophobic amino acid when $\sigma_2$ is a hydrophobic amino acid; $\epsilon_3$ is each independently one of glycine, alanine, valine, serine, threonine and asparagine when $\sigma_3$ is the fluorescent dye-bound molecule, and is each independently a hydrophobic amino acid when $\sigma_3$ is a hydrophobic amino acid; $X_1$, $X_4$ and $X_7$ are each any amino acid; and $X_M$ is a linker peptide containing M amino acids where M represents a number.

<15> The method according to <4>, wherein the polypeptide of the tag contains a sequence represented by the following structural formula (4) and the polypeptide of the probe contains a sequence represented by the following structural formula (5):

Tag:
$\{Ala-\gamma-\alpha-Lys-\beta-\gamma-Glu\}\{Ala-\epsilon_2-\alpha-Lys-\beta-\gamma-Glu\}$ (4)

$\{Ala-\gamma-\alpha-Lys-\beta-\gamma-Ala\}\{X_M\}\{Ala-\gamma-\beta-Lys-\beta-\gamma-Glu\}$ $\{Ala-\gamma-\beta-Lys-\beta-\epsilon_2-Glu\}\{Ala-\gamma-\beta-Lys-\beta-\gamma-Ala\}$

```
Probe:
{Ala-γ-α-Lys-α-γ-Glu}{Ala-γ-α-Lys-α-σ₂-Glu}     (5)

{Ala-γ-α-Lys-α-γ-Ala}
```

Wherein α is an acidic amino acid or a basic amino acid; B is a basic amino acid when α is an acidic amino acid, and is an acidic amino acid when α is a basic amino acid; γ is a hydrophobic amino acid; $\sigma_2$ is a molecule bound to a fluorescent dye; $\epsilon_2$ is each independently one of glycine, alanine, valine, serine, threonine and asparagine; and $X_M$ is a linker peptide contains M amino acids where M represents a number.

<16> The method according to <4>, wherein the polypeptide of the tag contains a sequence represented by the following structural formula (6) and the polypeptide of the probe contains a sequence represented by the following structural formula (7):

```
Tag:
{Ala-Leu-Lys-Lys-Glu-Leu-Glu}{Ala-ε₂-Lys-Lys-      (6)

Glu-Leu-Glu}{Ala-Leu-Lys-Lys-Glu-Leu-Ala}{X_M}

{Ala-Leu-Glu-Lys-Glu-Leu-Glu}{Ala-Leu-Glu-Lys-

Glu-ε₂-Glu}{Ala-Leu-Glu-Lys-Glu-Leu-Ala}

Probe:
{Ala-Leu-Lys-Lys-Lys-Leu-Glu}{Ala-Leu-Lys-Lys-    (7)

Lys-σ₂-Glu}{Ala-Leu-Lys-Lys-Lys-Leu-Ala}
``` wherein $\sigma_2$ is a molecule bound to a fluorescent dye; $\epsilon_2$ is each independently one of glycine, alanine, valine, serine, threonine and asparagine; and $X_M$ is a linker peptide containing M amino acids where M represents a number.

<17> The method according to any one of <1> to <16>, wherein the fluorescent dye is any of NBD (4-nitrobenzo-2-oxa-1,3-diazole), Dns (dansyl; 1-dimethylaminonaphthalene-5-sulfonyl), DAN (6-dimethylamino-2-naphthoyl), Ant (anthraniloyl), Mant (N-methylanthraniloyl), DMAP (4-dimethylaminophthalimide), DMAN (6-dimethylamino-2,3-naphthalimide), 3-dimethylaminobenzonitrile, ANS (1-anilinonaphthalene-8-sulfonic acid), MANS(N-methyl-2-anilinonaphthalene-6-sulfonic acid), TNS (2-p-toluidinylnaphthalene-6-sulfonic acid), dimethylaminophenoxazone, Nile Red, DAPDXYL SULFONYL (Registered trademark), indocyanine green, 7-hydroxycoumarin-3-carboxylic acid, 7-diethylaminocoumarin-3-carboxylic acid, fluorescein, 2,7-dichlorofluorescein, TAMRA (tetramethyl rhodamin), Cy3, Cy5, Cy7, coumarins, anthracene and pyrene.

<18> A tag bound to a target substance for use the method any one of <1> to <17> containing: a polypeptidepoypeptide forming an α-helix structure, the α-helix structure of the tag containing seven or more consecutive amino acid residues of an amino acid sequence represented by the following structural formula (1):

$$\{X_1—X_2—X_3—X_4—X_5—X_6—X_7\}_N \qquad (1)$$

wherein N is an integer of 2 or greater; $X_3$ and $X_5$ are each an acidic amino acid or a basic amino acid; $X_2$ and $X_6$ are each a hydrophobic amino acid; and $X_1$, $X_4$ and $X_7$ are each any amino acid.

<19> The tag according to <18>, wherein at least one of amino acid residues $X_2$ and $X_6$ present in at least one α-helix structure of the tag is substituted with one of glycine, alanine, valine, serine, threonine and asparagine.

<20> DNA encoding the tag according to any of <18> or <19>.

<21> A vector having the DNA according to <20> inserted therein.

<22> A probe for use in the method according to any one of <1> to <17>, containing: a polypeptide forming an α-helix structure, the α-helix structure of the probe containing seven or more consecutive amino acid residues of an amino acid sequence represented by the following structural formula (1):

$$\{X_1—X_2—X_3—X_4—X_5—X_6—X_7\}_N \qquad (1)$$

wherein N is an integer of 2 or greater; $X_3$ and $X_5$ are each an acidic amino acid or a basic amino acid; $X_2$ and $X_6$ are each a hydrophobic amino acid; and $X_1$, $X_4$ and $X_7$ are each any amino acid, and at least one of amino acid residues $X_2$ and $X_6$ present in at least one α-helix structure of the probe is substituted with a molecule bound to a fluorescent dye.

<23> A detection kit for a target substance, containing at least one of the tag according to any of <18> or <19>, the DNA according to <20>, and the vector according to <21>, along with the probe according to <22>.

According to the present invention, there is provided a method for detecting a target substance that can solve the above-described problems of prior art. Specifically, the present method can visualize the expression of the target substance at any time point while reducing influences on the functions of the target substance, can use fluorescent dyes having various excitation/emission wavelengths, and can achieve easy staining process. The present invention also provides a tag, a DNA, a vector, a probe and a detection kit suitable for use in the above-described detection method.

BRIEF DESCRIPTION OF THE SEVERAL VIEWS OF THE DRAWINGS

FIG. 3A shows the results of the circular dichroism spectroscopy performed for Example 1.

FIG. 4A shows the results of the fluorescence titration performed for Example 1.

FIG. 4C shows the results of the fluorescence titration performed for Example 3.

Figure 1:
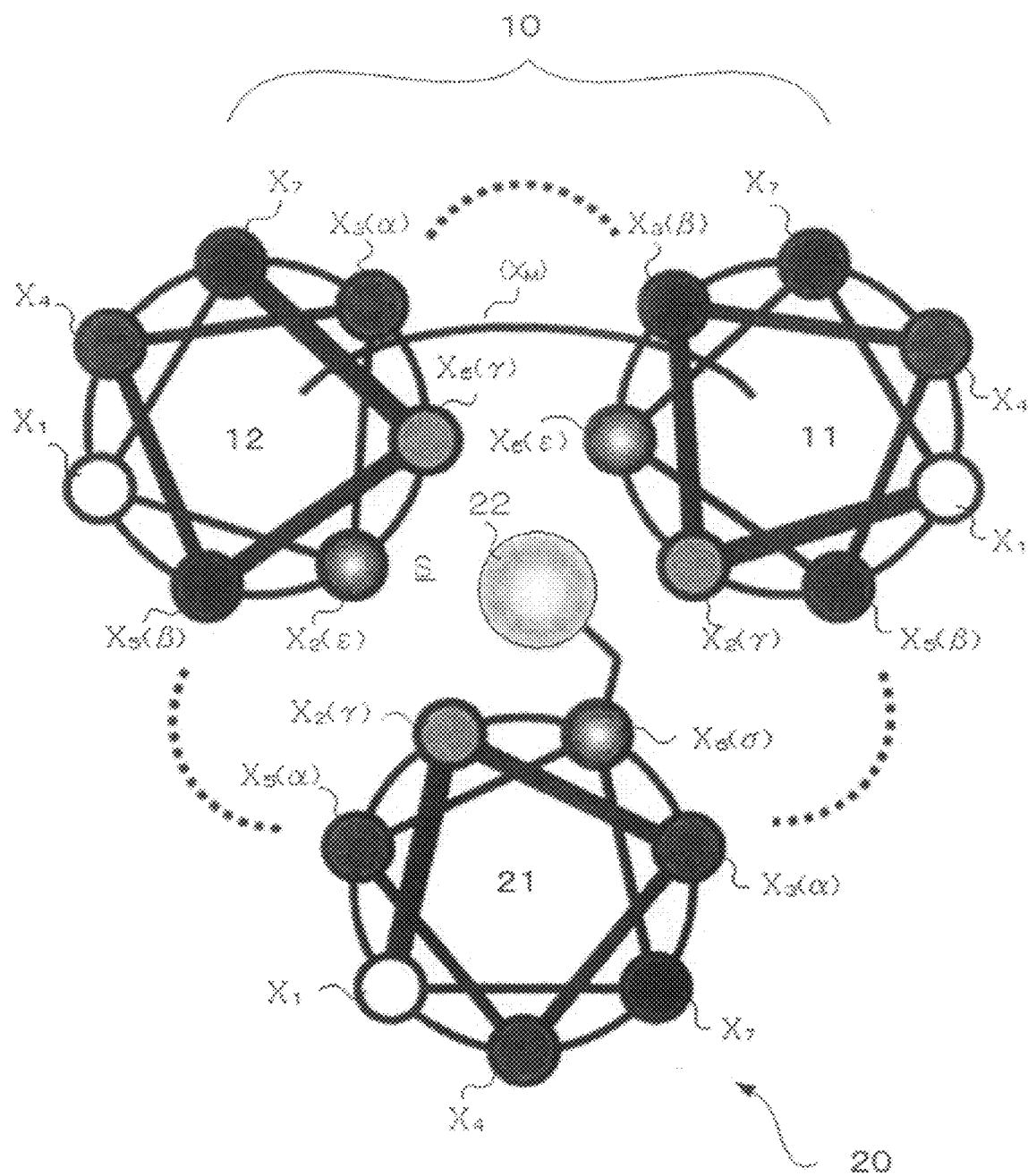
FIG. 1 shows α-helix structures formed by a tag and a probe of Specific Example, as viewed from the amino terminal end of the probe α-helix.

DETAILED DESCRIPTION OF THE INVENTION (Method for Detection of Target Substance)

A method for detecting a target substance in accordance with the present invention includes the following Steps 1 and 2, as well as other optional steps.

Step 1:

Bringing into contact with each other (a) a polypeptide tag forming an α-helix structure and bound to a target substance, and (b) a probe consisting of a compound bound to a fluorescent dye.

Step 2:

Measuring the Fluorescence Emitted by the Fluorescent Dye.

<Step 1>

(a) Tag

The tag for use in Step 1 is formed of a polypeptide that forms an α-helix structure and is bound to a target substance.

Hereinafter, the polypeptide to form the tag and the α-helix structure formed by the polypeptide are referred to as "tag polypeptide" and "tag α-helix structure," respectively, to distinguish from "probe polypeptide" and "probe α-helix structure," which will be described later.

Tag Polypeptide

The tag polypeptide may be any polypeptide that can form at least one α-helix structure. The tag polypeptide may be properly selected depending on the intended purpose: it may be a chemically synthesized polypeptide or a polypeptide expressed in a cell or cell-free system based on specific genetic information. When the target substance is a polypeptide, the tag polypeptide is preferably an expressed polypeptide and more preferably a polypeptide expressed by a cell system since such polypeptides are more convenient for constructing a tag-bound (i.e., tag-fused) target substance.

As used herein, the phrase "polypeptide that can form an α-helix structure" means that the tag polypeptide forms an α-helix structure at least when it forms a tag-probe complex. In other words, the tag polypeptide may or may not form an α-helix structure prior to contact with a probe. It is preferred, however, that the tag polypeptide form an α-helix structure even before it is brought into contact with a probe.

The tag polypeptide does not necessarily have to consist only of amino acids forming α-helix structures. It may also contain spacer peptides, linker peptides or any amino acid that does not form α-helix structures.

The tag polypeptide may be formed of any type of amino acids that are selected depending on the intended purpose. However, when the target substance is a polypeptide, it preferably consists of L-amino acids commonly expressed in a cell or cell-free system since such amino acids are more convenient for constructing a tag-bound (i.e., tag-fused) target substance.

While the tag polypeptide may consist of any suitable number of amino acid residues selected depending on the intended purpose, it preferably consists of 7 to 70 residues, more preferably 14 to 70 residues, and even more preferably 28 to 56 residues. If the polypeptide contains less than 7 amino acid residues, so does the α-helix structure and, as a result, the α-helix structure may become unstable or exhibit decreased binding affinity to the probe compound. Conversely, the polypeptide containing 70 or more amino acid residues may affect the structure and the function of the target substance.

The term "bound" as in "tag bound to a target substance" in Step 1 means that the tag and the target substance are bound to each other at a sufficient strength to ensure that the tag and the target substance do not dissociate from each other at least during Step 1 and Step 2. When the target substance is a polypeptide, the term specifically means that the tag is fused to the target substance (i.e., target polypeptide) on the amino terminal end, on the carboxyl terminal end, or in between via a peptide bond. The tag and the target polypeptide may be bound to each other either directly via a peptide bond or indirectly via an interposing spacer peptide containing several amino acids of.

Tag α-Helix Structure

The α-helix structure of the tag (i.e. tag α-helix structure) may be any α-helix structure as long as it can bind to the probe compound (including "probe α-helix structure," which will be described later) through hydrophobic interaction and a fluorescent dye can be placed in a hydrophobic environment formed through the hydrophobic interaction. Such a tag α-helix structure may be properly selected depending on the intended purpose. To further increase the binding affinity of the tag α-helix structure to the probe compound, it is preferred that the tag α-helix structure binds to the probe compound not only through the hydrophobic interaction, but also through electrostatic interaction. Such a tag α-helix structure can be formed by a specific amino acid sequence (i.e., primary structure).

The amino acid sequence to define the primary structure may be any amino acid sequence that can form an α-helix structure that meets the above-described requirements. Such an amino acid sequence may be appropriately selected depending on the intended purpose. Preferably, the amino acid sequence of the tag α-helix structure is as follows: it consists of seven or more consecutive amino acid residues of the amino acid sequence represented by the following structural formula (1):

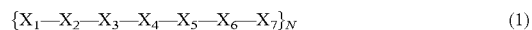

$$\{X_1-X_2-X_3-X_4-X_5-X_6-X_7\}_N \qquad (1)$$

wherein N is an integer of 2 or greater; $X_3$ and $X_5$ are each an acidic amino acid or a basic amino acid; $X_2$ and $X_6$ are each a hydrophobic amino acid; and $X_1$, $X_4$ and $X_7$ are each any amino acid.

More preferably, at least one of amino acid residues $X_2$ and $X_6$ present in at least one of the α-helix structures of the tag is substituted with any of glycine, alanine, valine, serine, threonine and asparagine.

The above-described acidic amino acid is a polar amino acid that is negatively charged at physiological pH while the above-described basic amino acid is a polar amino acid that is positively charged at physiological pH.

Specifically, the above-described acidic amino acid is glutamic acid or aspartic acid and the above-described basic amino acid is lysine or arginine. The above-described hydrophobic amino acid is leucine, isoleucine or valine. Each of repeating $X_1$ to $X_7$ may be the same amino acid or a different amino acid, provided that the above-described requirements are met.

Because $X_2$ and $X_6$ are each a hydrophobic amino acid, each of the tag α-helix structures has on its periphery two hydrophobic surfaces extending substantially along the longitudinal axis of the α-helix structure, so that each tag α-helix structure can bind to a probe compound having a hydrophobic surface and other α-helix structures of the tag through hydrophobic interaction.

The hydrophobic environment resulting from the hydrophobic interaction leads to the formation of hydrophobic pockets within which a fluorescent dye is to be placed.

In addition, the hydrophobic pockets within which a fluorescent dye is to be placed can be enlarged by substituting at least one of amino acid residues $X_2$ and $X_6$ present in at least in one of the α-helix structures of the tag with any of glycine, alanine, valine, serine, threonine and asparagine.

The shape and size of the hydrophobic pockets may be any shape that allows the fluorescent dye placed within the hydrophobic pockets to undergo spectral changes and may be appropriately selected depending on the intended purpose. In other words, the shape and size of the hydrophobic pockets may be properly adjusted depending on the shape or the size of the fluorescent dye or the binding distance between the fluorescent dye and the probe compound.

The shape and size of the hydrophobic pockets may be adjusted by changing the type, number and position of amino acids to be substituted. Specifically, a larger hydrophobic pocket can be obtained by substituting amino acids with shorter side chains, by substituting a greater number of amino acids, or by selecting positions of amino acid substitution so that a more extensive space is formed.

When the probe compound is a polypeptide forming an α-helix structure, the shape and size of the hydrophobic pocket can be adjusted by changing the total number of α-helix structures present in the tag-probe complex. Specifically, α-helix structures form a complex with the hydrophobic surface of each α-helix facing inward, so that a tag-probe complex containing a greater number of α-helix structures tends to form a polygonal arrangement with a more extensive space formed inside, hence, a larger hydrophobic pocket.

The total number of α-helix structures present in a tag-probe complex can be adjusted by changing the type of hydrophobic amino acids selected for $X_2$ and $X_6$.

By adjusting the shape and size of the hydrophobic pockets in the above-described manner, the tag-probe complex can be formed with higher complementarity and, correspondingly, spectral changes of the fluorescence emitted by the fluorescent dye will become more specific.

Because $X_3$ and $X_5$ are each an acidic or basic amino acid, each of the tag α-helix structures has on its periphery two independent negatively or positively charged surfaces extending substantially along the longitudinal axis of the α-helix structure, so that each tag α-helix structure can bind, through electrostatic interaction, to a probe compound having a correspondingly charged surface (i.e., positively charged surface for the negatively charged surface of the tag α-helix structure and negatively charged surface for the positively charged surface of the tag α-helix structure) or other α-helix structures of the tag.

The electrostatic interaction may be of any strength as long as the advantages of the present invention are not affected, and may be appropriately selected depending on the intended purpose. In general, however, stronger electrostatic interaction tends to result in stronger binding affinity between the tag α-helix structure and the probe compound. Specifically, electrostatic interaction increases in the order of aspartic acid and glutamic acid for the above-described acidic amino acids and in the order of lysine and arginine for the above-described basic amino acids.

By adjusting the electrostatic interaction in the above-described manner, the binding between the tag α-helix structure and the probe compound can be adjusted. This allows the tag-probe complex to be formed with higher complementarity and, as a result, the spectral changes of the fluorescence emitted by the fluorescent dye will become correspondingly more specific.

Since each tag α-helix structure contains seven or more amino acid residues, the tag α-helix structure is stabilized and becomes less susceptible to decomposition. The binding affinity of the tag α-helix structure to the probe compound is also increased.

While the tag α-helix structure preferably consists of 7 or more amino acid residues as described above, it is more preferred that the tag α-helix structure consist of 14 amino or more acid residues. When consisting of 14 or more amino acid residues, the tag α-helix structure is further stabilized and becomes even less susceptible to decomposition. The binding affinity of the tag α-helix structure to the probe compound is further increased.

The tag α-helix structures may be provided in any number as long as the advantages of the present invention are not affected. The number of the tag α-helix structures may be appropriately selected depending on the intended purpose. For example, one or two or more of the tag α-helix structures may be provided. When two or more of the tag α-helix structures are provided, they are preferably linked together via a peptide bond. While the tag α-helix structures may be linked together via a peptide bond either directly or indirectly through a linker peptide containing several amino acids, they are preferably linked together via a linker peptide.

The linker peptide may consist of any number of amino acid residues as long as the advantages of the present invention are not affected. The number of the amino acid residues to form the linker peptide may be properly selected depending on the intended purpose. Preferably, the linker peptide consists of 1 to 12 amino acid resides, and more preferably 5 to 7 amino acid residues. When the linker peptide contains 5 to 7 amino acid residues, it can appropriately form a loop structure that promotes antiparallel association of the linked α-helices.

(b) Probe

The probe for use in Step 1 consists of a compound bound to a fluorescent dye.

Fluorescent Dye

The fluorescent dye is placed in a space formed within the tag-probe complex. This not only prevents the solvent relaxation, but also suppresses the molecular motion, so that the quantum yield of fluorescence is increased and, thus, spectral changes of fluorescence are induced.

Examples of the spectral changes of fluorescence include changes in the wavelength of fluorescence and increases in the intensity of fluorescence.

Thus, the fluorescent dye may be any fluorescent dye and may be appropriately selected depending on the intended purpose. It is preferred, however, that the fluorescent dye be hydrophobic so that it can easily be placed in the hydrophobic environment formed by the tag-probe complex.

As described, the space formed within the complex is a hydrophobic environment. This is particularly desirable when the fluorescent dye is one that undergoes spectral changes in hydrophobic environment since significant spectral changes are induced in fluorescence when such a fluorescent dye is placed within the complex.

Examples of the fluorescent dyes that undergo spectral changes in hydrophobic environment include NBD (4-nitrobenzo-2-oxa-1,3-diazole), Dns (dansyl; 1-dimethylaminonaphthalene-5-sulfonyl), DAN (6-dimethylamino-2-naphthoyl), Ant (anthraniloyl), Mant (N-methylanthraniloyl), DMAP (4-dimethylaminophthalimide), DMAN (6-dimethylamino-2,3-naphthalimide), 3-dimethylaminobenzonitrile, ANS (1-anilinonaphthalene-8-sulfonic acid), MANS(N-methyl-2-anilinonaphthalene-6-sulfonic acid), TNS (2-p-toluidinylnaphthalene-6-sulfonic acid), dimethylaminophenoxazone, Nile Red and DAPDXYL SULFONYL (Registered trademark).

NBD in one measurement example shows fluorescence maximum at an excitation wavelength of 470 nm and an emission wavelength of 540 nm in hydrophilic environment and shows fluorescence maximum at an excitation wavelength of 456 nm and an emission wavelength of 505 nm in hydrophobic environment.

Dns in one measurement example shows fluorescence maximum at an excitation wavelength of 340 nm and an emission wavelength of 540 nm in hydrophilic environment and shows fluorescence maximum at an excitation wavelength of 340 nm and an emission wavelength of 503 nm in hydrophobic environment.

DAN in one measurement example shows fluorescence maximum at an excitation wavelength of 360 nm and an emission wavelength of 530 nm in hydrophilic environment and shows fluorescence maximum at an excitation wavelength of 360 nm and an emission wavelength of 400 nm in hydrophobic environment.

It should be understood that the characteristics of NBD, Dns and DAN are not limited to those shown for the above-described excitation wavelengths and emission wavelengths since the hydrophobicity of the same hydrophobic environment may vary depending on experimental conditions.

The fluorescent dye may bind to the probe compound at any binding site as long as the advantages of the present invention are not affected. Such a binding site may be appropriately selected depending on the intended purpose. It is preferred, however, that the fluorescent dye binds to the surface of the probe compound that binds to the tag α-helix structure through hydrophobic interaction.

One or more of the fluorescent dyes may bind to the probe compound. The number of the fluorescent dye that binds to the probe compound may be appropriately selected depending on the intended purpose.

Exemplary embodiments in which two or more fluorescent dyes are bound to the probe compound include those involving excimer emission and fluorescence resonance energy transfer (FRET).

In excimer emission, for example, a first pyrene molecule is placed on the surface of the probe compound that binds to the tag α-helix structure through hydrophobic interaction and a second pyrene molecule is bound to a different surface of the probe compound from the above-described surface. If only the probe molecules are present, then the first pyrene molecules and the second pyrene molecules can come close to each other without any interference and form dimers that emit fluorescence at a wavelength of 475 nm when exposed to excitation light with wavelength of 345 nm. In contrast, if both the probe molecules and the tag molecules are present, then the first pyrene molecules will be incorporated into the space formed within the tag-probe complex molecules, so that the first pyrene molecules are kept apart from the second pyrene molecules by a sufficient distance, leaving individual pyrene molecules as monomers. As a result, the wavelength of fluorescence that the pyrene molecules emit when exposed to excitation light with wavelength of 345 nm will shift to a wavelength of 375 nm.

In FRET, for example, a first fluorescent dye is placed on the surface of the probe compound that binds to the tag α-helix structure through hydrophobic interaction and a second fluorescent dye is bound to a different surface of the probe compound from the above-described surface. If only the probe molecules are present, then the first fluorescent dyes and the second fluorescent dyes can come close to each other without any interference, so that when the fluorescent dyes are exposed to light with excitation wavelength of the first fluorescent dye, energy transfer occurs from the first fluorescent dye to the second fluorescent dye due to resonance, causing the second fluorescent dye to emit fluorescence. In contrast, if both the probe molecules and the tag molecules are present, then the first fluorescent dyes will be incorporated into the space formed within the tag-probe complex molecules, so that the first fluorescent dyes are kept apart from the second fluorescent dyes by a sufficient distance. As a result, when the fluorescent dyes are exposed to light with excitation wavelength of the first fluorescent dye, the second fluorescent dyes will not emit fluorescence.

Examples of combinations of fluorescent dyes that can be used in FRET include NBD and 2,7-dichlorofluoroscein or Cy3; Dansyl and TAMRA (tetramethyl rhodamin); DAN and TAMRA or fluorescein; anthranilic acid and fluorescein; DMAP or DMAN and TAMRA; 7-dimethylamino-phenoxazine-3-one and Cy5; Nile Red and Cy7; 7-hydroxycoumarin-3-carboxylic acid, 7-diethylaminocoumarin-3-carboxylic acid or fluorescein and 7-dimethylamino-phenozazine-3-one; and 7-diethylaminocoumarin-3-carboxylic acid, fluorescein, 2,7-dichrolofluoresceín or Cy3 and Nile Red (In each combination, excitation of the former fluorescent dye causes the latter fluorescent dye to emit fluorescence).

Probe Compound

The compound (i.e., probe compound) may be any compound that can bind to the tag α-helix structure through hydrophobic interaction and can be used to place a fluorescent dye in the hydrophobic environment formed through the hydrophobic interaction. Such a compound may be appropriately selected depending on the intended purpose. To further increase the binding affinity of the probe compound to the tag α-helix structure, it is preferred that the probe compound bind to the tag α-helix structure through electrostatic interaction in addition to the hydrophobic interaction.

Examples of the probe compounds include α-helix-forming polypeptides and α-helix mimetic compounds. Of these, α-helix-forming polypeptides are particularly preferred since they can form a leucine zipper structure with the tag α-helix structure.

α-helix-forming polypeptides to serve as the probe compounds will now be described in detail.

The polypeptide to serve as the probe compound and the α-helix structure formed by the polypeptide are referred to as "probe polypeptide" and "probe α-helix structure," respectively, to distinguish from the above-described "tag polypeptide" and "tag α-helix structure."

Probe Polypeptide

The probe polypeptide may be any polypeptide that can form at least one α-helix structure. Such a polypeptide may be appropriately selected depending on the intended purpose: it may be a chemically synthesized polypeptide or a polypeptide expressed in a cell or cell-free system based on specific genetic information.

As used herein, the phrase "polypeptide that can form an α-helix structure" means that the probe polypeptide forms an α-helix structure at least when it forms a tag-probe complex. In other words, the probe polypeptide may or may not form an α-helix structure prior to contact with a tag. It is preferred, however, that the probe polypeptide form an α-helix structure even before it is brought into contact with a tag.

The probe polypeptide does not necessarily have to consist only of amino acids forming α-helix structures. It may also contain spacer peptides, linker peptides and any amino acid that does not form α-helix structures.

While the probe polypeptide may consist of any suitable number of amino acid residues selected depending on the intended purpose, it preferably consists of 7 to 42 residues, more preferably 14 to 42 residues, and even more preferably 14 to 28 residues. If the polypeptide contains less than 7 amino acid residues, so does the α-helix structure and, as a result, the α-helix structure may become unstable or exhibit decreased binding affinity to the tag α-helix structure. Conversely, the probe polypeptide containing 42 or more amino acid residues may not be effectively introduced into the cell through cell membrane, resulting in decreased efficiency and sensitivity of staining.

While the probe polypeptide may contain any amino acid properly selected depending on the intended purpose, it preferably consists of L-amino acids since much is known about L-amino acids, including the α-helix structure and the leucine zipper structure they form, and it therefore is easy to design probe polypeptides consisting of L-amino acids.

Probe α-Helix Structure

The α-helix structure of the probe (i.e. probe α-helix structure) may be any α-helix structure as long as it can bind to the tag α-helix structure through hydrophobic interaction and a fluorescent dye can be placed in a hydrophobic environment formed through the hydrophobic interaction. Such a probe α-helix structure may be properly selected depending on the intended purpose. To further increase the binding affinity of the probe α-helix structure to the tag α-helix structure, it is preferred that the probe α-helix structure binds to the tag α-helix structure not only through the hydrophobic interaction, but also through electrostatic interaction.

Such a probe α-helix structure can be formed by a specific amino acid sequence (i.e., primary structure).

The amino acid sequence to define the primary structure may be any amino acid sequence that can form an α-helix structure that meets the above-described requirements. Such an amino acid sequence may be appropriately selected depending on the intended purpose. Preferably, the amino acid sequence of the probe α-helix structure is as follows: it consists of seven or more consecutive amino acid residues of the amino acid sequence represented by the following structural formula (1):

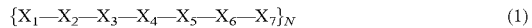

$$\{X_1-X_2-X_3-X_4-X_5-X_6-X_7\}_N \qquad (1)$$

wherein N is an integer of 2 or greater; $X_3$ and $X_5$ are each an acidic amino acid or a basic amino acid; $X_2$ and $X_3$ are each a hydrophobic amino acid; and $X_1$, $X_4$ and $X_7$ are each any amino acid, and at least one of amino acid residues $X_2$ and $X_6$ present in at least one of the α-helix structures of the probe is substituted with a specific molecule bound to a fluorescent dye.

The above-described acidic amino acid is a polar amino acid that is negatively charged at physiological pH while the above-described basic amino acid is a polar amino acid that is positively charged at physiological pH.

Specifically, the above-described acidic amino acid is glutamic acid or aspartic acid and the above-described basic amino acid is lysine or arginine. The above-described hydrophobic amino acid is leucine, isoleucine or valine. Each of repeating $X_1$ to $X_7$ may be the same amino acid or a different amino acid, provided that the above-described requirements are met.

Because $X_2$ and $X_6$ are each a hydrophobic amino acid, each of the probe α-helix structures has on its periphery two hydrophobic surfaces extending substantially along the longitudinal axis of the α-helix structure, so that each probe α-helix structure can bind to a tag α-helix structure having a hydrophobic surface and other α-helix structures of the probe through hydrophobic interaction.

In addition, the fluorescent dye is automatically arranged in the hydrophobic environment formed through the hydrophobic interaction by substituting at least one of amino acid residues $X_2$ and $X_6$ present in at least in one of the α-helix structures of the probe with the specific molecule bound to the fluorescent dye.

The above-described molecule bound to the fluorescent dye may be any molecule as long as it does not inhibit the formation of α-helix structures when substituted for the specific amino acid and incorporated into the probe α-helix structure. Such a molecule may be properly selected depending on the intended purpose. Examples of such molecules include L-amino acids having a fluorescent dye in the side chain, and diaminopropionic acid (Dap) having a fluorescent dye in the side chain.

The binding distance between the fluorescent dye and the probe α-helix structure can be adjusted by changing the number of carbon atoms in the side chain of the L-amino acid.

Because $X_3$ and $X_5$ are each an acidic or basic amino acid, each of the probe α-helix structures has on its periphery two independent negatively or positively charged surfaces extending substantially along the longitudinal axis of the α-helix structure, so that each probe α-helix structure can bind, through electrostatic interaction, to a tag α-helix structure having a correspondingly charged surface (i.e., positively charged surface for the negatively charged surface of the probe α-helix structure and negatively charged surface for the positively charged surface of the probe α-helix structure) or other α-helix structures of the probe.

The effects of electrostatic interaction are as described above with reference to the tag α-helix structure and will not be repeated here.

Since each probe α-helix structure contains seven or more amino acid residues, the probe α-helix structure is stabilized and becomes less susceptible to decomposition. The binding affinity of the probe α-helix structure to the tag α-helix structure is also increased.

While the probe α-helix structure preferably consists of 7 or more amino acid residues as described above, it is more preferred that the probe α-helix structure consist of 14 amino or more acid residues. When consisting of 14 or more amino acid residues, the probe α-helix structure is further stabilized and becomes even less susceptible to decomposition. The binding affinity of the probe α-helix structure to the tag α-helix structure is further increased.

When the probe contains two or more α-helix structures with at least one α-helix structure having no fluorescent dye bound thereto, it is preferred that at least one of amino acid residues $X_2$ and $X_6$ present in at least one of the α-helix structures be substituted with any of glycine, alanine, valine, serine, threonine and asparagine. In this manner, the shape and size of the hydrophobic pockets can be adjusted not only through the tags, but also through the probes.

The probe α-helix structures may be provided in any number as long as the advantages of the present invention are not affected. The number of the probe α-helix structures may be properly selected depending on the intended purpose. For example, one or two or more of the probe α-helix structures may be provided. When two or more of the probe α-helix structures are provided, they are preferably linked together via a peptide bond. While the probe α-helix structures may be linked together via a peptide bond either directly or indirectly through a linker peptide containing several amino acids of any type, they are preferably linked together via a linker peptide.

The linker peptide may consist of any number of amino acid residues as long as the advantages of the present invention are not affected. The number of the amino acid residues to form the linker peptide may be properly selected depending on the intended purpose. Preferably, the linker peptide consists of 1 to 12 amino acid resides, and more preferably 5 to 7 amino acid residues. When the linker peptide contains 5 to 7 amino acid residues, it can appropriately form a loop structure that promotes antiparallel association of the linked α-helices.

Quenchers

In addition to the fluorescent dye, a quencher and other optional components may be bound to the probe compound depending on the embodiment of the present invention.

In one embodiment involving the use of a quencher, for example, the quencher is placed on the surface of the probe compound that binds to the tag α-helix structure through hydrophobic interaction and a fluorescent dye is bound to a different surface of the probe compound from the above-described surface. If only the probe molecules are present, then the quencher molecules and the fluorescent dye molecules can come close to each other without any interference. As a result, fluorescence is not emitted when the fluorescent dye is exposed to light with an excitation wavelength for the fluorescent dye. In contrast, if both the probe molecules and the tag molecules are present, then the quencher molecules will be incorporated into the space formed within the tag-probe complex molecules, so that the quencher molecules are kept apart from the fluorescent dye molecules by a sufficient distance to prevent the quencher from suppressing the emission of the fluorescent dye. As a result, fluorescence is emitted when the fluorescent dye is exposed to light with an excitation wavelength for the fluorescent dye.

Examples of the quencher include nitrobenzene derivatives, Dabcyl derivatives and QSY. Examples of the fluorescent dye that can be used in combination with the quenchers include coumarins, anthracene and pyrene.

In Step 1, (a) tag and (b) probe may be brought into contact with each other using any suitable technique that is selected depending on the intended purpose. Typically, a solution containing (b) probe is added to a solution containing (a) tag so that (a) tag and/or (b) probe can diffuse in the solution and come into contact with each other.

When necessary, other steps may be involved, including incubation step and stirring step for thoroughly reacting (a) tag and (b) probe. As long as the advantages of the present invention are not affected, the incubation step may be carried out under any suitable condition with regard to temperature, time or atmosphere. However, the step is preferably carried out at a temperature of 37° C. for a time period of 0.5 to 1 hour in a 5% $CO_2$ atmosphere.

When (a) tag is localized in cells, organs or living body and it is desired to bring into contact (a) tag with (b) probe in situ, the step of injecting the probe into cells, organs or living body by transformation, transfection, conjugation, protoplast fusion, electroporation, particle guns, calcium phosphate precipitation, microinjection, endocytosis by membrane-permeable peptides and other techniques may be involved.

In Step 1, the tag α-helix structure and the probe compound are bound together through hydrophobic interaction and/or electrostatic interaction to form a tag-probe complex, as described above. The tag-probe complex may be of any suitable form as long as the advantages of the present invention are not affected. Such a form may be properly selected depending on the intended purpose.

For example, when the probe compound is a polypeptide forming an α-helix structure, the tag-probe complex may contain any suitable number of α-helices that is selected depending on the desired purpose. However, the tag-probe complex consists preferably of dimer to pentamer, more preferably of trimer or tetramer of α-helix structures. The α-helices may be oriented either parallel or antiparallel to each other.

Avidin or biotin may be bound to the tag and probe so that the formation of tag-probe complexes through hydrophobic interaction and/or electrostatic interaction will be enhanced by the avidin-biotin binding. Alternatively, free SH groups, such as cysteine side chains, may be incorporated in the tag and probe so that the formation of tag-probe complexes through hydrophobic interaction and/or electrostatic interaction will be enhanced by disulfide linkages. Similarly, antigen/antibody, diazo-bonds, gold/thiol, crosslink reaction and other bindings may be employed to enhance the formation of tag-probe complexes through hydrophobic interaction and/or electrostatic interaction. Of these, the crosslink reaction is particularly preferred since it allows tags and probes to be reacted at desired timing and reversibly bonded via covalent bonds after mixed together and is therefore suitable for use with pulse-chase analysis.

By using any of the above-described techniques, the fluorescent dye is automatically arranged in the hydrophobic environment formed through the hydrophobic interaction. Once placed in the hydrophobic environment, the fluorescent dye undergoes spectral changes: it is induced to exhibit at least a shift in emission wavelength or an increase in fluorescence intensity.

As used herein, "a shift in emission wavelength" means that different emission wavelengths are detected for the same excitation wavelength before and after Step 1. As used herein, "an increase in fluorescence intensity" means that an increase in fluorescence intensity is observed when the fluorescent dye is exposed to fluorescence having the same wavelength before and after Step 1. Preferably, the fluorescent dye is exposed to the same excitation wavelength before and after Step 1.

On the other hand, the fluorescent dye bound to the probes that do not form the tag-probe complexes is not placed in the hydrophobic environment and therefore does not undergo spectral changes in Step 1. This can be distinguished from the fluorescent dye that has undergone spectral changes in response to the formation of the tag-probe complexes. Accordingly, only the fluorescent dye bound to the probes that have formed tag-probe complexes can be detected without washing the excess probes after (a) tag and (b) probe are brought into contact in Step 1.

One embodiment will now be described in which the crosslink reaction is used to perform pulse-chase analysis.

Fluorescent dyes that emit different wavelengths are bound to a first probe and a second probe. Functional groups having crosslink activity are also added to the probes. An expression vector is constructed by ligating a DNA fragment encoding a tag-fused target polypeptide downstream of a constitutively expressing promoter. The expression vector is introduced into cells and the cells are cultured.

The first probe is added to the cells expressing the target polypeptide and is allowed to crosslink with the tag. When necessary, the cells are exposed to UV radiation to promote crosslinking. Since the tag is irreversibly bound to the probe through the crosslink reaction, the target polypeptide labeled with the first probe can no longer be labeled with the second probe.

The cells are continuously cultured and stimulated to cause changes in the localization of the target polypeptide.

Subsequently, the second probe is added to the cells and is allowed to crosslink with the tag. When necessary, the cells are exposed to UV radiation to promote crosslinking. The second probe cannot label the target polypeptide labeled with the first probe, but labels only newly expressed target polypeptide.

When the cells are observed by a fluorescence microscope, different localization of the target polypeptide labeled with the first probe and the target polypeptide labeled with the second probe is confirmed.

<Step 2>

In Step 2, the fluorescence emitted by the fluorescent dye whose fluorescence spectrum has changed in Step 1 is measured.

In Step 2, the fluorescence may be measured by any suitable means including a known spectrofluorometer.

The fluorescence may be measured in Step 2 under any condition as long as the advantages of the present invention are not affected. Such condition may be properly selected depending on the intended purpose. For example, the excitation wavelength to irradiate the fluorescent dye and the emission wavelength emitted by the fluorescent dye may be a single wavelength or different wavelengths.

The excitation wavelength to irradiate the fluorescent dye and the emission wavelength emitted by the fluorescent dye may be any suitable wavelength that can measure the fluorescence emitted by the fluorescent dye whose fluorescence spectrum changes before and after Step 1. Such a wavelength may be properly selected depending on the intended purpose.

For example, when the fluorescence of NBD is measured at an excitation wavelength of 456 nm and an emission wavelength of 505 nm, the detected fluorescence intensity increases about 18 times during Step 1 and can therefore serve as a suitable measure of tag-probe complex formation.

For example, when the fluorescence of Dns is measured at an excitation wavelength of 340 nm and an emission wavelength of 503 nm, the detected fluorescence intensity increases about 15 times during Step 1 and can therefore serve as a suitable measure of tag-probe complex formation.

In Step 2, the measurement of fluorescence may be taken as many times as necessary. The suitable number of times of measurement may be selected depending on the intended purpose. For example, the measurement may be taken only once, multiple times, or over time.

In Step 2, the measurement of fluorescence may be taken at any time point, given that the fluorescence is measured at least at the end of Step 1. Such a time point may be properly selected depending on the intended purpose. It is preferred, however, that the measurement be also taken before Step 1 for comparison of the fluorescence between before and after Step 1.

<Subject of Detection>

Target Substance

The target substance to be detected by the method of the present invention may be any substance that is properly selected depending on the intended purpose, including polypeptides, nucleic acids, sugars, lipids and other biological molecules. Of these, polypeptides are preferred since they can easily be fused with the tags. The above-described polypeptides include antibodies and the above-described lipids include liposomes.

Hereinafter, the target substances formed of polypeptides will be referred to as "target polypeptides" and will now be described in detail.

The target polypeptides are polypeptides consisting of two or more amino acids that are bonded together via peptide bonds.

The target polypeptide may be any suitable polypeptide that is selected depending on the intended purpose. For example, it may be a chemically synthesized polypeptide or a polypeptide expressed in a cell or cell-free system based on specific genetic information. Preferably, the target polypeptide is an expressed polypeptide since such polypeptides are more convenient for constructing a tag-bound (i.e., tag-fused) target polypeptide. More preferably, the target polypeptide is a polypeptide expressed by a cell system since its kinetics and functions in the cells can be directly studied. The polypeptide expressed in the cell system may be a polypeptide whose expression level in a living body changes over time, or it may be a constitutively expressed polypeptide.

The target polypeptide may be of any suitable origin that is selected depending on the intended purpose: it may be an artificially designed polypeptide, a naturally occurring polypeptide or a modified polypeptide thereof.

The target polypeptide itself may be a fusion polypeptide fused with a known tag peptide, a fluorescent protein or a reporter protein. For example, the target polypeptide may be a fusion polypeptide fused with histidine tag, green fluorescent protein (GFP), luciferase or FLAG tag.

The target polypeptide may be formed of any type of amino acids that is selected depending on the intended purpose. However, it preferably consists of L-amino acids commonly expressed in a cell or cell-free system since such amino acids are more convenient for constructing a tag-fused (i.e., tag-bound) target polypeptide.

While the target polypeptide may consist of any suitable number of amino acid residues selected depending on the intended purpose, it preferably consists of 2 to 1000 residues, and more preferably 50 to 1000 residues. Thus, the target polypeptide encompasses dipeptides, tripeptides, oligopeptides, polypeptides and proteins.

In one preferred embodiment of the detection method of the present invention, the tag-fused target polypeptide is introduced for detection purpose into a living body in which one desires to observe the kinetics or the functions of the target polypeptide (such as organisms, organs, tissues, cells of interest, as described below).

When the tag-fused target polypeptide is an antibody, the probe of the present invention may be used as a secondary antibody to label a primary antibody. Thus, an antibody fused with the tag of the present invention may be used in combination with the probe of the present invention to provide a useful research tool.

Subject Organism

The tag-fused target polypeptide may be introduced into any suitable organism (i.e., subject organism) that is selected depending on the intended purpose, including bacteria, yeast, plants, insects, birds, reptiles, amphibians and mammals Subject Organ The tag-fused target polypeptide may be introduced into any suitable organ (i.e., subject organ) that is selected depending on the intended purpose, including embryo, skin, blood vessel, cornea, kidney, heart, liver, umbilical cord, intestine, nerve, lung, placenta, pancreas, brain, distal portions of the extremities, retina and other organs.

Subject Tissue

The tag-fused target polypeptide may be introduced into any suitable tissue (i.e., subject tissue) that is selected depending on the intended purpose, including epithelial tissue, connective tissue, muscle tissue and nerve tissue.

Subject Cell

The tag-fused target polypeptide may be introduced into any suitable cell (i.e., subject cell) that is selected depending on the intended purpose, including epidermal cells, pancreatic parenchymal cells, pancreatic ductal cells, liver cells, blood cells, cardiac muscle cells, skeletal muscle cells, osteoblasts, skeletal myoblasts, nerve cells, vascular endothelial cells, pigment cells, smooth muscle cells, fat cells, bone cells, chondrocytes, egg cells, ES cells and other cells. The cells may be those existing in a living body or they may be cultured cells or cells isolated from a living body.

Introduction Technique

The tag-fused target polypeptide may be introduced into a living body in which one desires to observe the kinetics or the functions of the target polypeptide by using any suitable technique that is selected depending on the intended purpose. Examples of such techniques include transformation, transfection, conjugation, protoplast fusion, electroporation, particle guns, calcium phosphate precipitation, microinjection, endocytosis by membrane-permeable peptides and other techniques. The tag-fused target polypeptide may be introduced into a living body either as a polypeptide or as polypeptide-encoding DNA that expresses the polypeptide in a living body.

(Tag)

The tag of the present invention is bound to the above-described target substance for use in the method for detecting the target substance. Specifically, the tag is formed of a polypeptide forming an α-helix structure as described above with reference to the method for detecting a target substance.

Production Method

The tag for use in the present invention may be produced by any suitable method selected depending on the intended purpose. For example, the tag may be chemically synthesized or it may be expressed in a cell or cell-free system based on specific genetic information. The chemical synthesis may be carried out by any suitable technique selected depending on the intended purpose: for example, the synthesis may be carried out by various solid or liquid phase synthesis techniques, such as the fluorenyl-methoxy-carbonyl (Fmoc) method or the tert-butyl oxy carbonyl method (Boc) method.

The expression based on specific genetic information may be carried out by using any suitable technique selected depending on the intended purpose. For example, using a known genetic engineering technique, a DNA fragment may be constructed by ligating a tag-encoding gene downstream of a promoter. The resulting DNA fragment may be introduced into cells by a known technique or mixed with a cell-free reaction mixture containing RNA polymerase, adenosine triphosphate (ATP), ribosome, amino acids and other components for expression. The resulting tag may be used as a tag either directly or after purification.

In order for a tag to be expressed based on specific genetic information, a DNA fragment is preferably constructed that contains a promoter, and a gene encoding a tag and a gene encoding a target polypeptide ligated downstream of the promoter. In this manner, the tag can be expressed as a fusion polypeptide.

(DNA)

The DNA of the present invention contains a base sequence encoding the above-described tag, as well as other optional base sequences.

The base sequences encoding the tag may be those that were described above with reference to the tag.

Examples of other base sequences include promoter sequences located upstream of the tag-encoding base sequence, terminator sequences located downstream of the tag-encoding base sequence, and polyA signals. The promoter sequence may be one that can express the tag-encoding base sequence in desired host cells. The DNA of the present invention may also contain other base sequences such as enhancers, marker genes for selecting the cells carrying the DNA, and restriction sites for inserting a gene encoding a target polypeptide into the DNA of the present invention.

(Vector)

The vector of the present invention has the above-described DNA inserted therein and may include other optional components.

The DNA may be one that was described above with reference to the tag-encoding DNA.

The vector may be any suitable vector typically selected depending on the type of host cells to express the vector and the techniques used for gene introduction. Prokaryotic vectors, eukaryotic vectors, animal cell vectors and plant cell vectors are preferred and known in the art. When the expression in animal cells is desired, viral vectors may be used. Examples of other components include protein particles and cells for packaging viral vectors.

(Probe)

The probe of the present invention is used for the method for detecting a target substance. Specifically, the probe consists of a compound bound to the fluorescent dye described above with reference to the method for detecting a target substance. As described above, examples of the probe compounds include polypeptides forming an α-helix structure, mimetic compounds of an α-helix structure and other compounds. Of these, polypeptides forming an α-helix structure are particularly preferred since they can form a leucine zipper structure with the tag α-helix structure.

Production Method

Fluorescent dyes can be obtained from the following sources: NBD is available in the form of NBD chloride from chemical reagent distributers such as Kanto Chemical, Tokyo Chemical Industry and Aldrich. Dns is available in the form of Dns chloride from chemical reagent distributers such as Kanto Chemical, Tokyo Chemical Industry, Wako Pure Chemical Industries and Sigma-Aldrich. DAN can be produced according to techniques described in literature (See, for example, Bruce E. Cohen, et al., Science, 2002, 296, 1700-1703). Fluorescent dyes whose spectrum changes in a hydrophobic environment, such as Ant (anthraniloyl), Mant (N-methylanthraniloyl), DMAP (4-dimethylaminophthalimide), DMAN (6-dimethylamino-2,3-naphthalimide), 3-dimethylaminobenzonitrile, ANS (1-anilinonaphthalene-8-sulfonic acid), MANS(N-methyl-2-anilinonaphthalene-6-sulfonic acid), TNS (2-p-toluidinylnaphthalene-6-sulfonic acid), dimethylaminophenoxazone, Nile Red and DAPDXYL SULFONYL (Registered trademark), can be produced by various synthetic techniques. For example, NBD chloride or Dns chloride can be reacted with L-amino acids having an amino side chain to produce L-amino acids having the fluorescent dye in the side chain.

The above-described probe polypeptides may be produced by any suitable technique selected depending on the intended purpose. For example, the probe polypeptides may be chemically synthesized or they may be expressed in a cell or cell-free system based on specific genetic information.

The chemical synthesis may be carried out by any suitable technique selected depending on the intended purpose: for example, the synthesis may be carried out by various solid or liquid phase synthesis techniques, such as the fluorenyl-methoxy-carbonyl (Fmoc) method or the tert-butyl oxy carbonyl (Boc) method.

For example, an L-amino acid having a fluorescent dye in the side chain may be incorporated in place of amino acids during the chemical synthesis to produce a probe.

The expression based on specific genetic information may be carried out by using any suitable technique selected depending on the intended purpose. For example, using a known genetic engineering technique, a DNA fragment may be constructed by ligating a tag-encoding gene downstream of a promoter. The resulting DNA fragment may be introduced into cells by a known technique or mixed with a cell-free reaction mixture containing RNA polymerase, adenosine triphosphate (ATP), ribosome, amino acids and other components for expression.

The expressed polypeptides are purified and reacted with a fluorescent dye having a reaction group selective for a specific amino acid (for example, cysteine) to allow the fluorescent dye to bind to the specific amino acid and, thus, form a probe.

(Detection Kit for Target Substance)

The kit for detecting a target substance in accordance with the present invention contains at least one of the tag, the DNA and the vector, along with the probe.

<Specific Example>

One specific example of the present embodiment will now be described. It should be understood, however, that the present invention is not limited to this example in any way.

In Specific Example, the tag polypeptide and the probe polypeptide are represented by the following structural formulas (2) and (3), respectively:

Tag:
$\{X_1-\epsilon_1-\alpha-X_4-\beta-\gamma-X_7\}\{X_1-\epsilon_2-\alpha-X_4-\beta-\gamma-X_7\}\{X_1-\epsilon_3-\alpha-X_4-\beta-\gamma-X_7\}\{X_M\}\{X_1-\gamma-\beta-X_4-\beta-\epsilon_3-X_7\}\{X_1-\gamma-\beta-X_4-\beta-\epsilon_2-X_7\}\{X_1-\gamma-\beta-X_4-\beta-\epsilon_1-X_7\}$ (2)

Probe:
$\{X_1-\gamma-\alpha-X_4-\alpha-\sigma_1-X_7\}\{X_1-\gamma-\alpha-X_4-\alpha-\sigma_2-X_7\}\{X_1-\gamma-\alpha-X_4-\alpha-\sigma_3-X_7\}$ (3)

wherein
 α is an acidic amino acid or a basic amino acid;
 β is a basic amino acid when α is an acidic amino acid, and is an acidic amino acid when α is a basic amino acid;
 γ is a hydrophobic amino acid;
 at least one of $\sigma_1$ to $\sigma_3$ is a molecule bound to a fluorescent dye and the rest of $\sigma_1$ to $\sigma_3$ are each a hydrophobic amino acid;
 $\epsilon_1$ is each independently one of glycine, alanine, valine, serine, threonine and asparagine when $\sigma_1$ is the fluorescent dye-bound molecule, and is each independently a hydrophobic amino acid when of is a hydrophobic amino acid;
 $\epsilon_2$ is each independently one of glycine, alanine, valine, serine, threonine and asparagine when $\sigma_2$ is the fluorescent dye-bound molecule, and is each independently a hydrophobic amino acid when $O_2$ is a hydrophobic amino acid;
 $\epsilon_3$ is each independently one of glycine, alanine, valine, serine, threonine and asparagine when $\sigma_3$ is the fluorescent dye-bound molecule, and is each independently a hydrophobic amino acid when $\sigma_3$ is a hydrophobic amino acid;
 $X_1$, $X_4$ and $X_7$ are each any amino acid; and
 $X_M$ is a linker peptide consisting of M amino acids.

FIG. 1 shows α-helix structures formed by the tag and probe of Specific Example, as viewed from the amino terminal end of the probe α-helix.

In Specific Example, the polypeptide of the tag 10 forms two α-helix structures 11, 12 linked by a linker peptide ($X_M$), whereas the polypeptide of the probe 20 forms a single α-helix structure 21, as shown in FIG. 1.

In each of the α-helix structures 11, 12 and 21, amino acids ε ($\epsilon_1$ to $\epsilon_3$), a ($\sigma_1$ to $\sigma_3$) and γ are faced inward toward the center of the tag-probe complex through hydrophobic interaction and are arranged in proximity to one another to form a hydrophobic environment in the center of the complex (not shown).

The amino acids α and β in each of the α-helix structures 11, 12 and 21 are designed to carry electrical charges that correspond to the electrical charges of adjacent α-helix structures 11, 12 and 21, so that the resulting electrostatic interaction (indicated by dotted lines in FIG. 1) can further increase binding affinity and thus stabilize the complex.

Each amino acid ε in the α-helices 11, 12 of the tag 10 has been substituted with a short side-chain amino acid and is positioned opposite amino acid a bound to the fluorescent dye 22 to ensure a large hydrophobic pocket S for containing the fluorescent dye 22.

As a result, the fluorescent dye 22, bound to amino acid a in the α-helix structure 21 of the probe 20, is automatically arranged within the hydrophobic pocket S.

Figure 2:
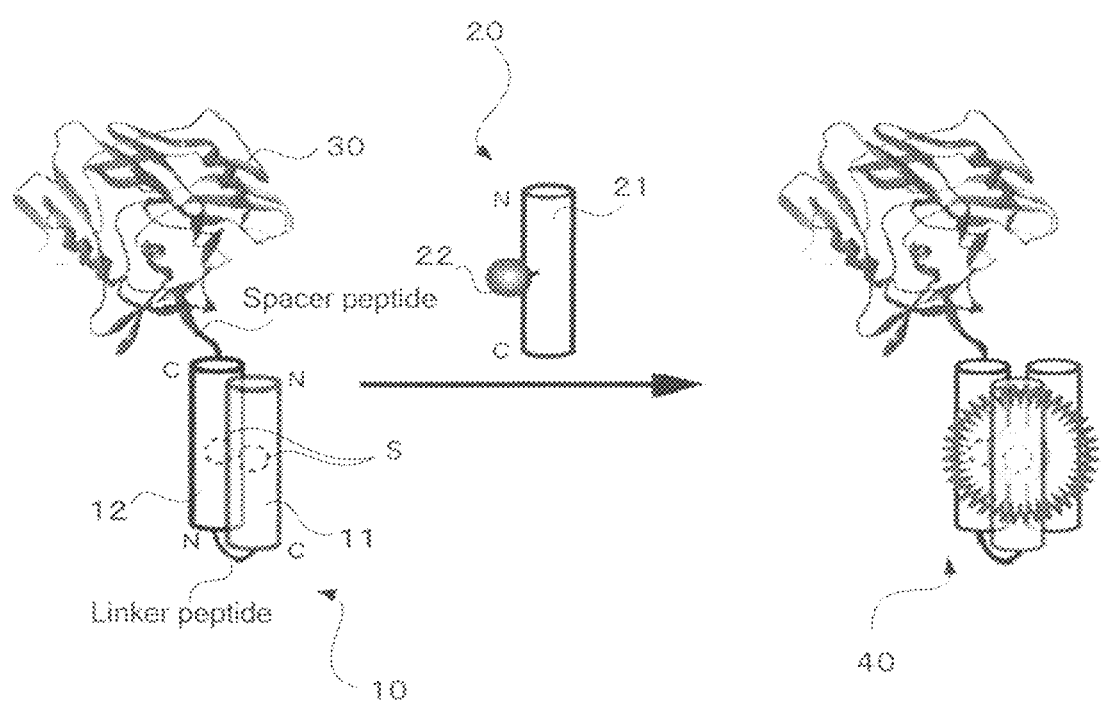
FIG. 2 illustrates the concept of one method of Specific Example for detecting a target substance.

FIG. 2 illustrates the concept of the method of Specific Example for detecting a target substance.

As shown in FIG. 2, the α-helix structures 11, 12 of tag 10 and the α-helix structure 21 of probe 20 are bound together through hydrophobic and electrostatic interaction to form a tag-probe complex 40. As a result, the fluorescent dye 22 is automatically arranged in a hydrophobic environment (i.e., hydrophobic pocket S) formed through the hydrophobic interaction. The fluorescent dye 22, once placed in the hydrophobic environment, undergoes spectral changes. Specifically, the dye is induced to exhibit at least a shift in emission wavelength or an increase in fluorescence intensity. As a result, the fluorescence specific for the formation of the tag-probe complex 40 can be detected. In Specific Example shown in FIG. 2, the presence of target substance 30 can be detected by detecting the specific fluorescence since the target substance 30 is bound to the tag 10.

In Specific Example, it is more preferred that the tag polypeptide and the probe polypeptide be represented by the following structural formulas (4) and (5), respectively:

Tag:
$\{Ala-\gamma-\alpha-Lys-\beta-\gamma-Glu\}\{Ala-\epsilon_2-\alpha-Lys-\beta-\gamma-Glu\}$ (4)

$\{Ala-\gamma-\alpha-Lys-\beta-\gamma-Ala\}\{X_M\}\{Ala-\gamma-\beta-Lys-\beta-\gamma-Glu\}$ $\{Ala-\gamma-\beta-Lys-\beta-\epsilon_2-Glu\}\{Ala-\gamma-\beta-Lys-\beta-\gamma-Ala\}$ Probe:
$\{Ala-\gamma-\alpha-Lys-\alpha-\gamma-Glu\}\{Ala-\gamma-\alpha-Lys-\alpha-\sigma_2-Glu\}$ (5)

$\{Ala-\gamma-\alpha-Lys-\alpha-\gamma-Ala\}$ wherein
 α is an acidic amino acid or a basic amino acid;
 β is a basic amino acid when α is an acidic amino acid, and is an acidic amino acid when α is a basic amino acid;
 γ is a hydrophobic amino acid;
 $\Gamma_2$ is a molecule bound to a fluorescent dye;
 $\epsilon_2$ is each independently one of glycine, alanine, valine, serine, threonine and asparagine; and
 $X_M$ is a linker peptide consisting of M amino acids.

Amino acids arranged in the tag and the probe having the respective structural formulas (4) and (5) have high tendency to form an α-helix. Specifically, the tag and the probe having the structural formulas (4) and (5) are more likely to form a tag-probe complex as compared to the tag and the probe having the structural formulas (2) and (3).

In Specific Example, it is even more preferred that the tag polypeptide and the probe polypeptide be represented by the following structural formulas (6) and (7), respectively:

Tag:
{Ala-Leu-Lys-Lys-Glu-Leu-Glu}{Ala-$\epsilon_2$-Lys-Lys-   (6)

Glu-Leu-Glu}{Ala-Leu-Lys-Lys-Glu-Leu-Ala}{X$_M$}

{Ala-Leu-Glu-Lys-Glu-Leu-Glu}{Ala-Leu-Glu-Lys-

Glu-$\epsilon_2$-Glu}{Ala-Leu-Glu-Lys-Glu-Leu-Ala}

Probe:
{Ala-Leu-Lys-Lys-Lys-Leu-Glu}{Ala-Leu-Lys-Lys-    (7)

Lys-$\sigma_2$-Glu}{Ala-Leu-Lys-Lys-Lys-Leu-Ala} wherein
   $\sigma_2$ is a molecule bound to a fluorescent dye;
   $\epsilon_2$ is each independently one of glycine, alanine, valine, serine, threonine and asparagine; and
   X$_M$ is a linker peptide consisting of M amino acids.
   Amino acids arranged in the tag and the probe having the respective structural formulas (6) and (7) have high tendency to form an α-helix. Specifically, the tag and the probe having the structural formulas (6) and (7) are more likely to form a tag-probe complex as compared to the tag and the probe having the structural formulas (4) and (5).

EXAMPLES

The present invention will now be described with reference to examples, which are not intended to limit the present invention in any way.

Example 1

In Example 1, a tag polypeptide and a probe polypeptide were synthesized that are represented by the following structural formulas (8) and (9), respectively. In the figure, the tag polypeptide and the probe polypeptide are indicated as "A2" and "L-NBD," respectively.

Tag:
                                    (SEQ ID No: 1)
{Ala-Leu-Lys-Lys-Glu-Leu-Glu}{Ala-Ala-Lys-Lys-   (8)

Glu-Leu-Glu}{Ala-Leu-Lys-Lys-Glu-Leu-Ala}{Gly-

Gly-Cys-Gly-Gly}{Ala-Leu-Glu-Lys-Glu-Leu-Glu}

{Ala-Leu-Glu-Lys-Glu-Ala-Glu}{Ala-Leu-Glu-Lys-

Glu-Leu-Ala}

Probe:
                                    (SEQ ID NO: 2)
{Ala-Leu-Lys-Lys-Lys-Leu-Glu{Ala-Leu-Lys-Lys-    (8)

Lys-Dap(NBD)-Glu}{Ala-Leu-Lys-Lys-Lys-Leu-Ala}

<Synthesis Technique>
The synthesized peptides are separated and purified by high performance liquid chromatography (HPLC) and identified by matrix-assisted laser desorption/ionization time-of-flight mass spectrometry (MALDI-TOF-MS).
PLC was performed using LaChrom Elite HTA system (Hitachi High-Technologies) with a 5C$_{18}$-AR-II analysis column (4.6×250 mm, Nacalai Tesque) and a 5C$_{18}$-AR-II semi-preparative column (10×250 mm, Nacalai Thsque) for purification. 0.1% trifluoroacetic acid in ultrapure water (Solvent A) and high purity acetonitrile (Solvent B) were used as eluents in HPLC. Specifically, the proportions of Solvent A and Solvent B were continuously changed to elute the target peptide. The peptide was detected by Ultraviolet-visible spectroscopy (measured at 220 nm wavelength).
MALDI-TOF-MS was performed using Voyager DE-STR (Applied Biosystems). To 5 μl of the HPLC peptide eluate, 5 μl of an α-cyano-4-hydroxycinnamic acid solution (10 mg/mL in 50:50 H$_2$O/CH$_3$CN (acetonitrile), 0.1% trifluoroacetic acid) were added to form a sample solution. 2 μl of the sample solution were spotted on a sample plate to prepare a sample for measurement. The measuring instrument was corrected using a peptide (protein) of known molecular weight and the signal of the target peptide was detected as a protonated form ([M+H]$^+$).

Synthesis of Probe Peptide
According to the Fmoc solid phase synthesis technique described in literature (W. C. Chan, P. D. White, in Fmoc Solid Phase Peptide Synthesis: A Practical Approach; Eds., W. C. Chan, P. D. White, Oxford University Press Inc., New York, 2000, 41.), the probe peptide was elongated by stepwise coupling of the Fmoc protecting amino acid on a resin.
45 mg (0.025 mmol) of Rink Amide resin with a incorporation rate of amino group at 0.55 mmol/g resin were placed in a reaction tube and washed and swelled in N,N-dimethylformamide (DMF). The resin was stirred and agitated in a piperidine (PPD)/DMF solution for 15 minutes and was subsequently washed 6 times with 2 mL DMF. 5 equivalents (relative to amino group) of Fmoc protecting amino acid, diisopropylcarbodiimide (5 equivalents), N-hydroxybenzotriazole monohydrate (5 equivalents) were dissolved in 2 mL DMF. The solution was stirred and agitated for 1 hour and was subsequently washed 6 times with 2 mL DMF. In this manner, the amino acids were sequentially coupled to elongate the peptide chain.
After elongation, the amino groups on the amino terminals were acetylated with 50 equivalents of acetic anhydride in 2 mL DMF. The resin was then washed with chloroform and dried in vacuum. To the acetylated peptide-resin, 0.1 ml m-cresol, 0.3 mL thioanisole, 0.04 mL triisopropylsilane and 4 mL trifluoroacetic acid were added and the mixture was stirred at room temperature for 1 hour. Subsequently, the reaction mixture was filtered and the filtrate was concentrated under reduced pressure. To the resulting residue, ice-cooled diethyl ether was added to form a precipitate. The precipitate was centrifuged (at 3000 rpm), washed several times with diethyl ether, and dried in vacuum to obtain crude peptide. The crude peptide was then dissolved in a 10% aqueous acetic acid solution and was purified by HPLC using a C18 reversed-phase semi-preparative column (10×250 mm). The purified product was concentrated under reduced pressure and freeze-dried to give 3.51 mg of the desired probe peptide at 5% yield.
HPLC (gradient: AB=78/22→48/52, 30 min)
Elution time=15.1 min
[M+H]$^+$=2685.6 (Calcd [M+H]$^+$=2685.2)
Synthesis of Tag Peptide
Two fragments (Chain A and Chain B) were synthesized separately and linked together to synthesize the tag peptide. Chain A and Chain B were divided by a cysteine residue of a linker peptide. The fragment having the cysteine was designated as Chain A and the other fragment was designated as Chain B.
Chain A was synthesized and purified in the same manner as the probe peptide.
For Chain B, a first amino acid was introduced onto a 2-chlorotrityl chloride resin and the elongation was carried out on the resin in the same manner as the probe peptide. The elongated peptide was cleaved from the resin in a solution containing acetic acid/trifluoroethanol/dichloromethane at a ratio of 1/1/3. The solution was concentrated under reduced pressure and dried in vacuum. The resulting protected crude peptide was thioesterified using 1-ethyl-3-(3-dimethylaminopropyl)carbodiimide hydrochloride (EDCl.HCl), N-hydroxybenzotriazole monohydrate and ethyl mercaptopropionate. The resulting thioester was deprotected under the same condition used for the probe peptide and purified by HPLC.

Using the native chemical ligation method, the purified Chain A and Chain B were linked together in a denaturing condition with guanidine in a phosphate buffered saline at pH7.4. This gave the desired tag peptide at a yield of 8%.

HPLC (gradient: A/B=70/30→40/60, 30 min)
Elution time=23.5 min
[M+H]$^+$=5309.8 (Calcd [M+H]$^+$=5309.1)

Example 2

In Example 2, a tag polypeptide and a probe polypeptide were synthesized using the same synthesis procedure as in Example 1.

The tag polypeptide and the probe polypeptide synthesized in Example 2 are represented by the following structural formulas (10) and (9), respectively. The probe polypeptide was identical to that of Example 1. In the figure, the tag polypeptide and the probe polypeptide are indicated as "L2" and "L-NBD," respectively.

```
Tag:
                                          (SEQ ID NO: 3)
{Ala-Leu-Lys-Lys-Glu-Leu-Glu}{Ala-Leu-Lys-    (10)

Lys-Glu-Leu-Glu}{Ala-Leu-Lys-Lys-Glu-Leu-Ala}

{Gly-Gly-Cys-Gly-Gly}{Ala-Leu-Glu-Lys-Glu-

Leu-Glu}{Ala-Leu-Glu-Lys-Glu-Leu-Glu}{Ala-

Leu-Glu-Lys-Glu-Leu-Ala}

Probe:
                                          (SEQ ID NO: 2)
{Ala-Leu-Lys-Lys-Lys-Leu-Glu}{Ala-Leu-Lys-    (9)

Lys-Lys-Dap(NBD)-Glu}{Ala-Leu-Lys-Lys-Lys-

Leu-Ala}
```

Example 3

In Example 3, a tag polypeptide and a probe polypeptide were synthesized using the same synthesis procedure as in Example 1.

The tag polypeptide and the probe polypeptide synthesized in Example 3 are represented by the following structural formulas (11) and (9), respectively. The probe polypeptide was identical to that of Example 1. In the figure, the tag polypeptide and the probe polypeptide are indicated as "G2" and "L-NBD," respectively.

```
Tag:
                                          (SEQ ID NO: 4)
{Ala-Leu-Lys-Lys-Glu-Leu-Glu}{Ala-Gly-Lys-    (11)

Lys-Glu-Leu-Glu}{Ala-Leu-Lys-Lys-Glu-Leu}

{Gly-Gly-Cys-Gly-Gly}{Ala-Leu-Glu-Lys-Glu-

Leu-Glu}{Ala-Leu-Glu-Lys-Glu-Gly-Glu}{Ala-

Leu-Glu-Lys-Glu-Leu-Ala}
```

```
Probe
                                          (SEQ ID NO: 2)
{Ala-Leu-Lys-Lys-Lys-Leu-Glu}{Ala-Leu-Lys-    (9)

Lys-Lys-Dap(NBD)-Glu}{Ala-Leu-Lys-Lys-Lys-

Leu-Ala}
```

Example 4

Circular Dichroism Spectroscopy

The circular dichroism spectrum of the tag polypeptides and the probe polypeptides of Examples 1 to 3 were measured.

The structures of the tag peptide, the probe peptide and the tag-probe complex were analyzed by circular dichroism spectroscopy. Specifically, circular dichroism spectroscopy was performed on Jasco J-720WI spectropolarimeter (Jasco) using a quartz cell having an optical path length of 1 cm.

Figure 3B:
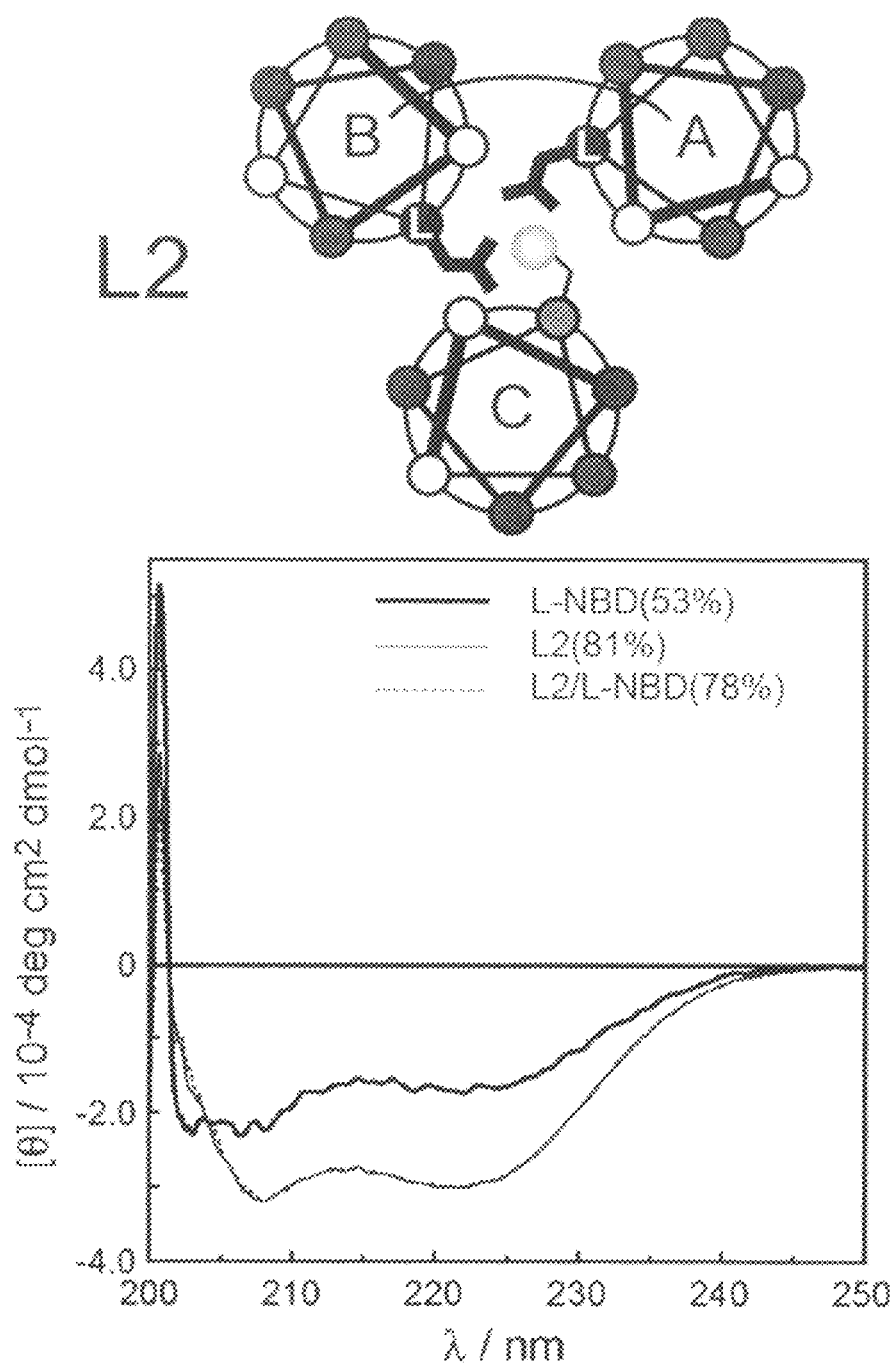
FIG. 3B shows the results of the circular dichroism spectroscopy performed for Example 2.
Figure 3C:
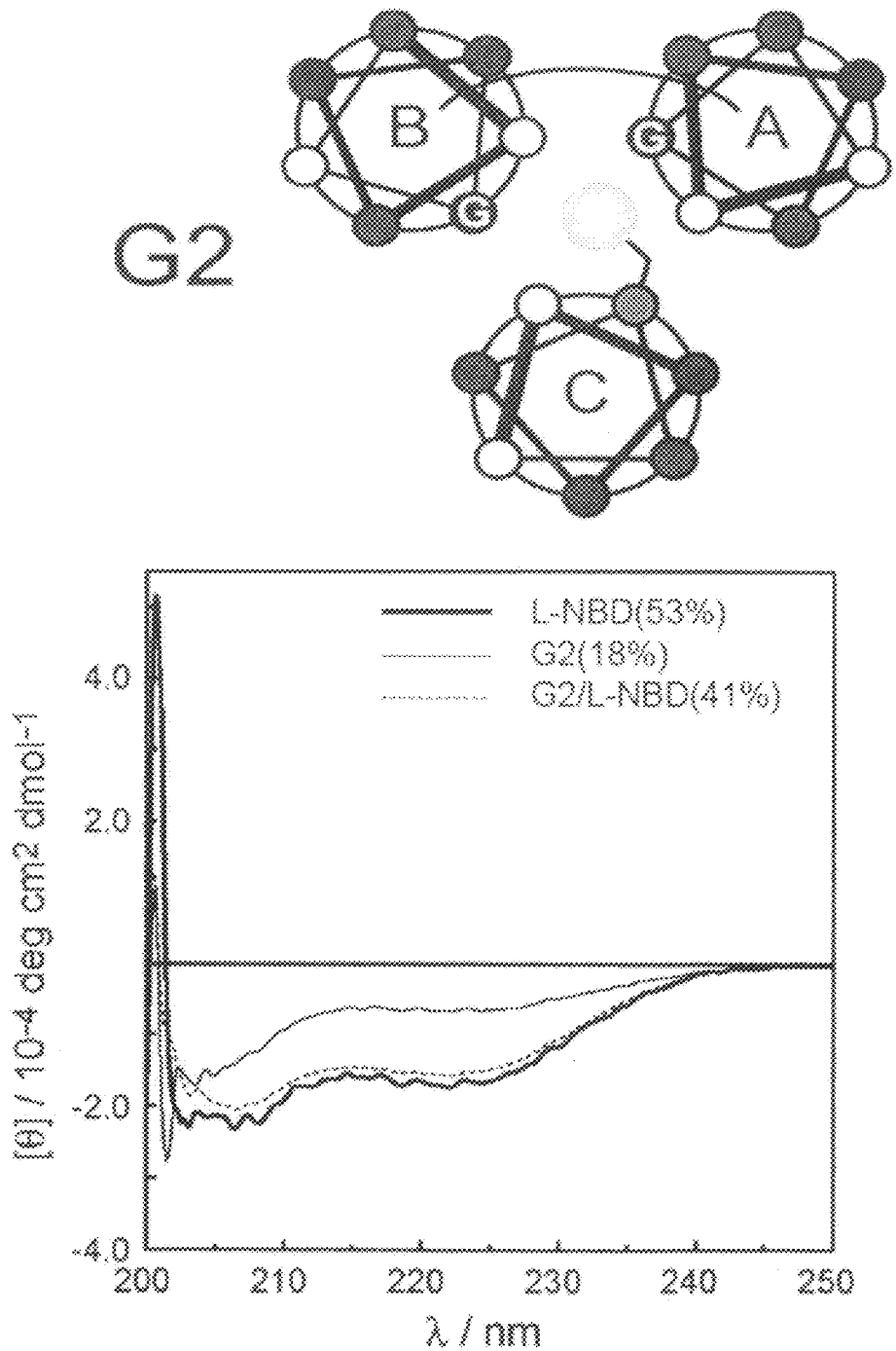
FIG. 3C shows the results of the circular dichroism spectroscopy performed for Example 3.

FIG. 3A shows the results of the circular dichroism spectroscopy performed for Example 1. FIG. 3B shows the results of the circular dichroism spectroscopy performed for Example 2. FIG. 3C shows the results of the circular dichroism spectroscopy performed for Example 3. In each of FIGS. 3A to 3C, the horizontal axis represents wavelength used for measurement whereas the vertical axis represents molar residue ellipticity.

FIG. 3A indicates that 58% of the tag peptides and 53% of the probe peptides formed an α-helix structure in Example 1. The figure also indicates that more tags and probes (71%) formed an α-helix structure in the tag-probe mixture.

FIG. 3B indicates that 81% of the tag peptides and 53% of the probe peptides formed an α-helix structure in Example 2. The figure also indicates that more tags and probes (78%) formed an α-helix structure in the tag-probe mixture.

FIG. 3C indicates that 18% of the tag peptides and 53% of the probe peptides formed an α-helix structure in Example 3. The figure also indicates that more tags and probes (41%) formed an α-helix structure in the tag-probe mixture.

Example 5

Fluorescence Titration

Fluorescence titration was performed for the tag polypeptides and the probe polypeptides of Examples 1 to 3.

To 0.5 μM of a probe peptide solution (HEPES buffer), 0.1 to 2.0 equivalents of a tag peptide solution were added dropwise and the fluorescence spectrum was measured. Specifically, the fluorescence spectroscopy was performed on Jasco FP-750 spectrofluorometer (Jasco) using a quartz cell having an optical path length of 1 cm.

Figure 4B:
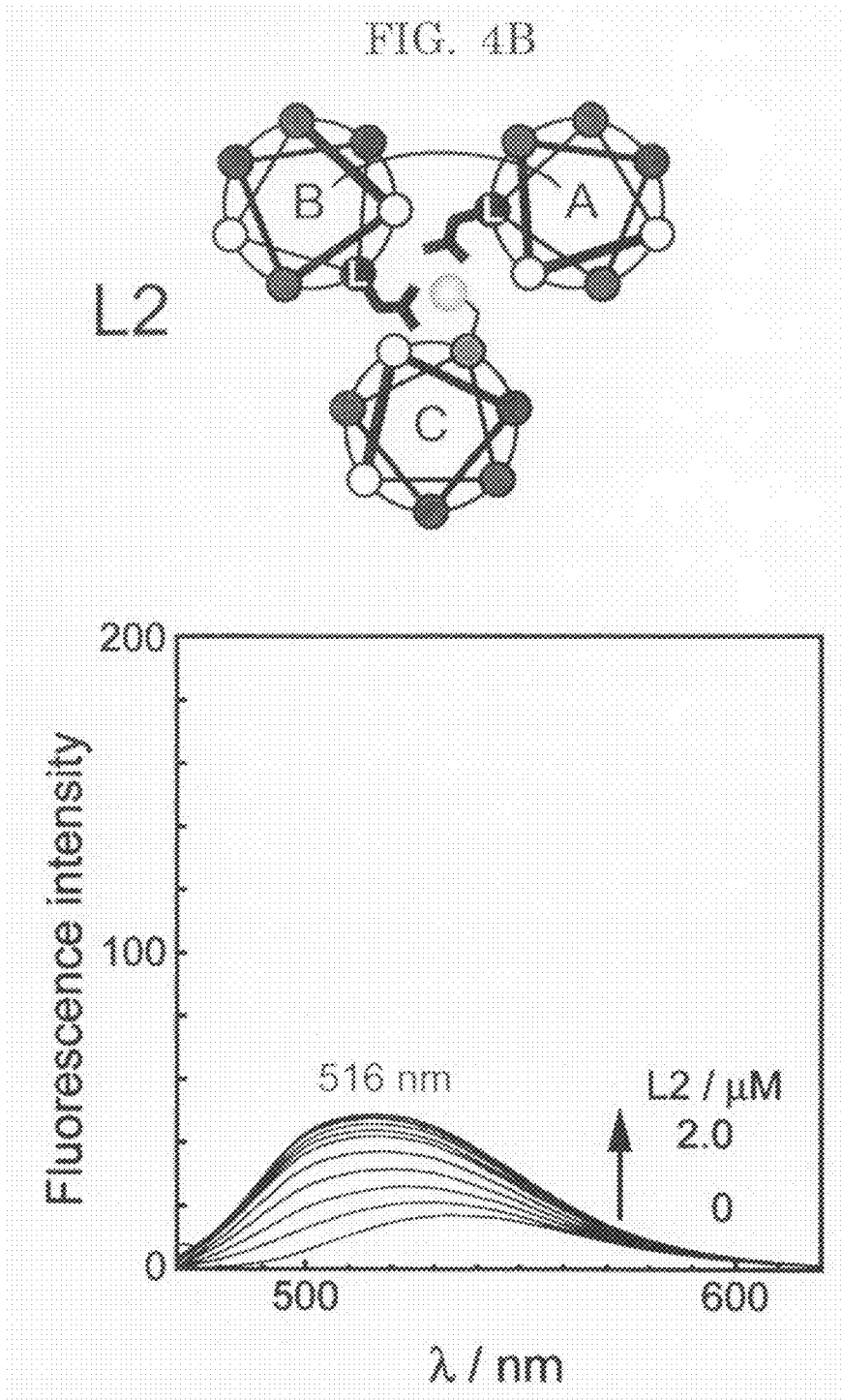
FIG. 4B shows the results of the fluorescence titration performed for Example 2.

FIG. 4A shows the results of the fluorescence titration performed for Example 1. FIG. 4B shows the results of the fluorescence titration performed for Example 2. FIG. 4C shows the results of the fluorescence titration performed for Example 3. In each of FIGS. 4A to 4C, the horizontal axis represents the wavelength of fluorescence whereas the vertical axis represents intensity of fluorescence.

FIG. 4A indicates that in Example 1, relatively weak fluorescence was detected near 540 nm for the probe peptide alone, and as the concentration of the tag peptide was increased, the fluorescence wavelength was shifted to shorter wavelengths and the fluorescence intensity increased significantly. The fluorescence wavelength ultimately shifted to as short a wavelength as 505 nm.

FIG. 4B indicates that in Example 2, relatively weak fluorescence was detected near 540 nm for the probe peptide alone, and as the concentration of the tag peptide was increased, the fluorescence wavelength was shifted to shorter wavelengths and the fluorescence intensity increased significantly. The fluorescence wavelength ultimately shifted to as short a wavelength as 516 nm.

FIG. 4C indicates that in Example 3, relatively weak fluorescence was detected near 540 nm for the probe peptide alone, and as the concentration of the tag peptide was increased, the fluorescence wavelength was shifted to shorter wavelengths and the fluorescence intensity increased significantly. The fluorescence wavelength ultimately shifted to as short a wavelength as 526 nm.

Figure 5:
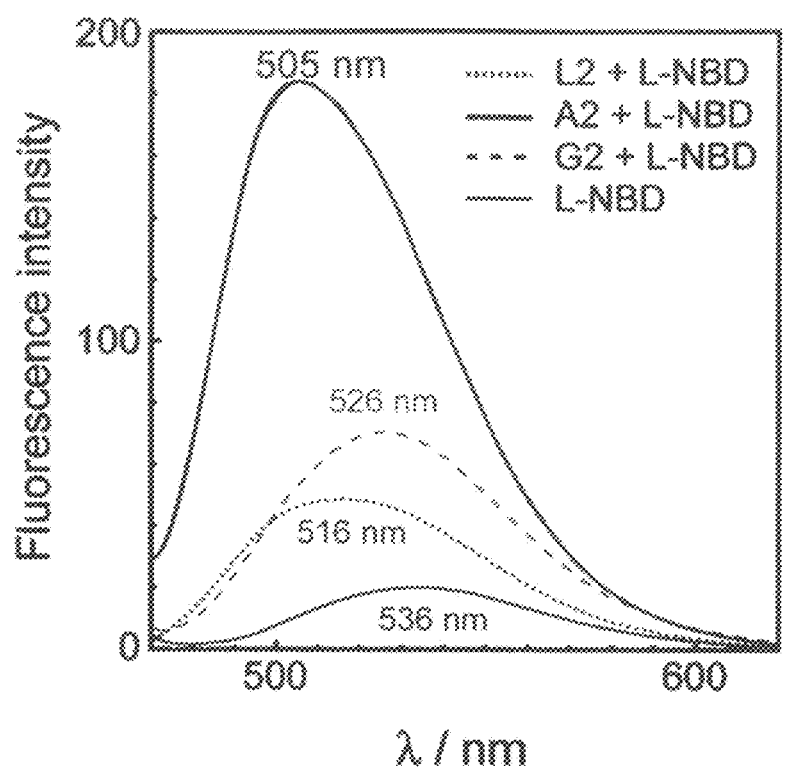
FIG. 5 shows the overlapped fluorescence spectra for the highest peaks of fluorescence intensity shown in FIGS. 4A to 4C.

FIG. 5 shows the overlapped fluorescence spectra for the highest peaks of fluorescence intensity shown in FIGS. 4A to 4C.

As shown in FIG. 5, a comparison of Examples 1 to 3 indicates that the combination of the tag peptide and the probe peptide of Example 1 exhibits the highest fluorescence intensity.

In the fluorescence titration, the rate of change of the fluorescence intensity at 505 nm was plotted against the concentration of the tag peptide and the dissociation constant was calculated from a theoretical formula assuming 1 to 1 binding of the tag peptide to the probe peptide.

Figure 6:
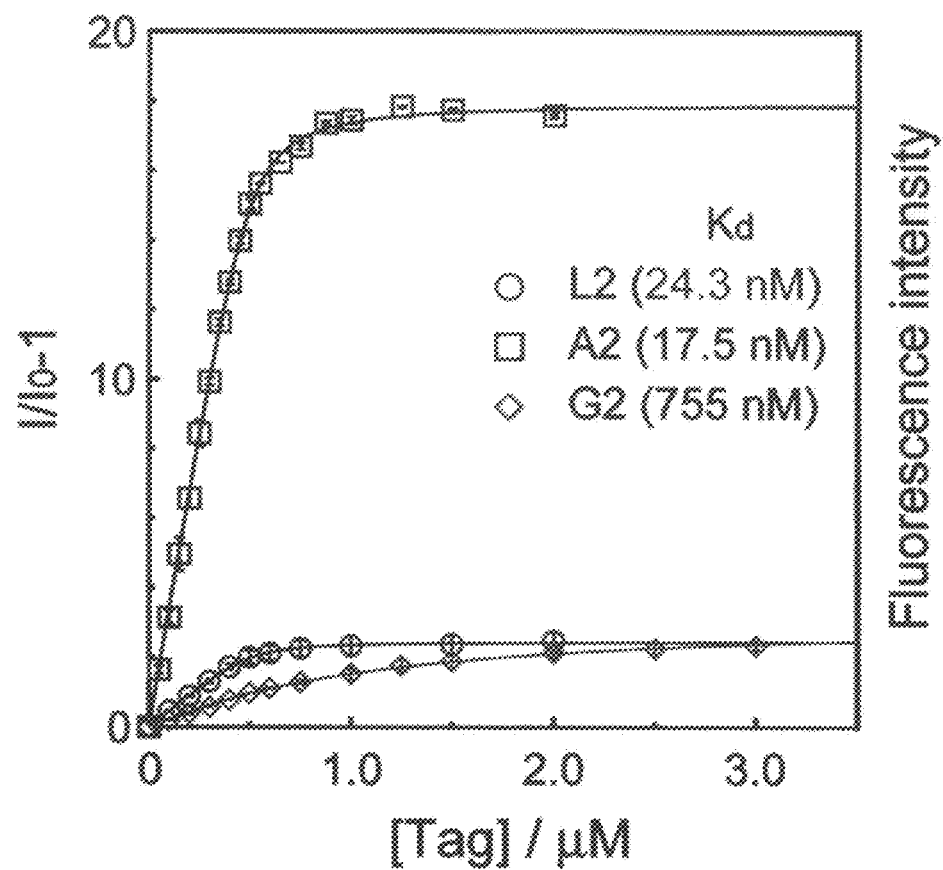
FIG. 6 shows the results of fluorescence titration.

FIG. 6 shows the results of fluorescence titration. In FIG. 6, the horizontal axis represents the titer of the tag against the probe whereas the vertical axis represents the relative increase in fluorescence intensity when the fluorescence intensity detected for the probe alone at fluorescence wavelength of 505 nm is estimated as 1. As shown in FIG. 6, the changes in fluorescence reached saturation at 1 equivalent of tag peptide in each of Examples 1 to 3. In Example 1, the fluorescence intensity at 505 nm in the presence of 1 equivalent of tag peptide was 18 times as high as that measured in the absence of the tag peptide. The dissociation constant Kd was determined to be 17.5 nM by analyzing the change in fluorescence using the theoretical formula assuming 1 to 1 interaction of the tag peptide to the probe peptide. This indicates that the interaction between the tag and the probe peptides exhibits binding affinity comparable at least to binding affinity of antibodies. Likewise, the dissociation constants Kd for Examples 2 and 3 were determined to be 24.3 nM and 755 nM, respectively.

Also in the fluorescence titration, with the total concentration of the tag peptide and the probe peptide being fixed at 1.0 µM, the ratio of the respective concentrations of the tag peptide and the probe peptide was varied and the fluorescence intensity at 505 nm was measured. The measured fluorescence intensity was plotted against the ratio of the tag peptide concentration to the total concentration of the tag peptide and the probe peptide and was analyzed by the theoretical formula assuming 1 to 1 binding of the tag peptide to the probe peptide.

Figure 7:
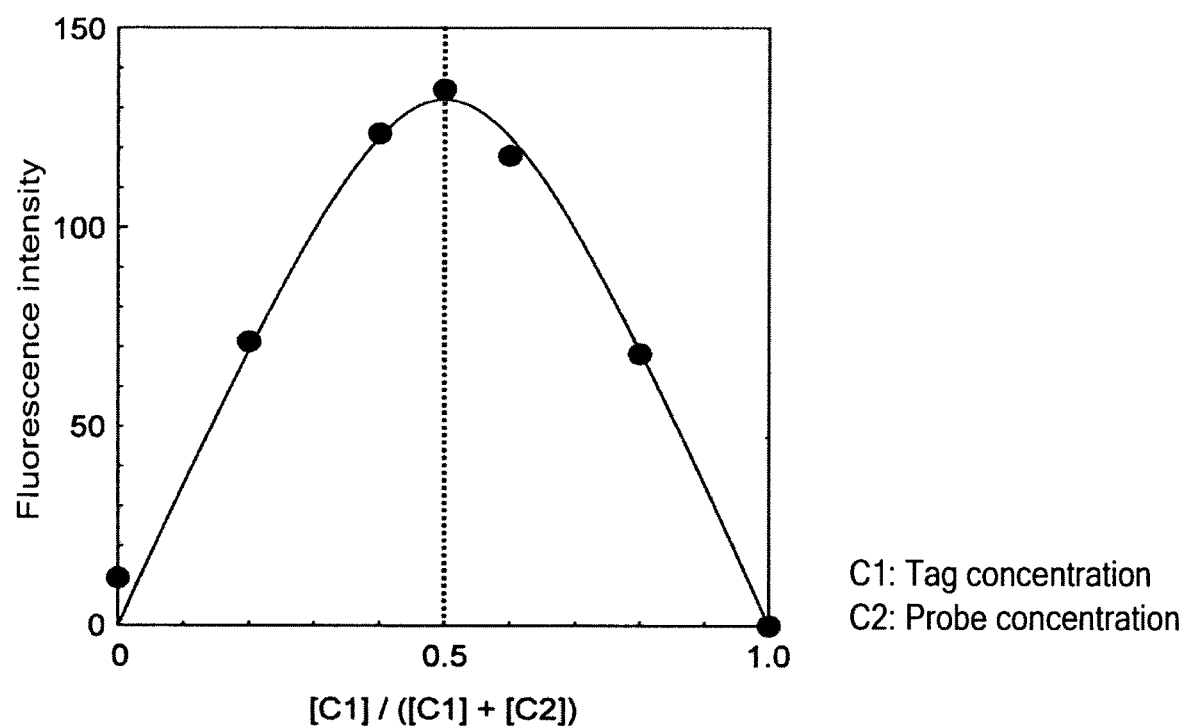
FIG. 7 shows a Job's plot for the tag peptide and the probe peptide of Example 1.

FIG. 7 is a Job's plot for the tag peptide and the probe peptide of Example 1. In FIG. 7, the horizontal axis represents the ratio of the concentration of the tag peptide to the total concentration of the tag peptide and the probe peptide, and the vertical axis represents the fluorescence intensity at 505 nm. FIG. 7 indicates 1:1 interaction of the tag peptide and the probe peptide, suggesting that the two α-helices present in a single tag peptide associate with one α-helix present in a single probe peptide to form an α-helix trimer.

Example 5

Comparison with BSA

The tag polypeptide and the probe polypeptide of Example 1 were compared with BSA.

To 0.5 µM of a probe peptide solution (HEPES buffer), 1 to 100 equivalents of a tag peptide solution or a BSA solution were added dropwise and the fluorescence spectrum was measured. Specifically, the fluorescence spectroscopy was performed on Jasco FP-750 spectrofluorometer (Jasco) using a quartz cell having an optical path length of 1 cm.

Figure 8:
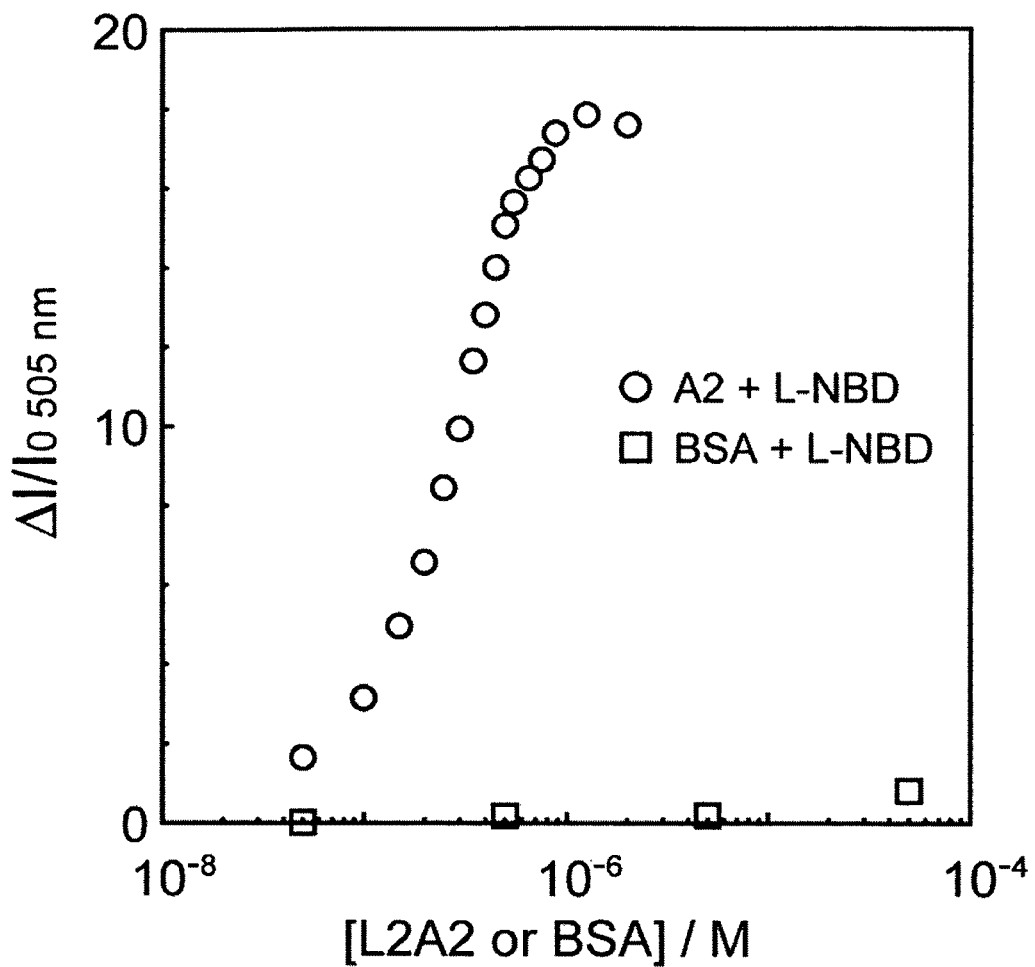
FIG. 8 shows the results of Example 5.

FIG. 8 shows the results of Example 5. In FIG. 8, the horizontal axis represents the titer of the tag or BSA against the probe whereas the vertical axis represents the relative increase in fluorescence intensity when the fluorescence intensity detected for the probe alone at fluorescence wavelength of 505 nm is estimated as 1. FIG. 8 indicates that the fluorescence spectrum changed little by the addition of 100 equivalents of BSA to the probe peptide. This demonstrates that either the probe peptide does not bind to BSA, or if it does, the binding brings about no change in fluorescence.

Example 6

Fluorescence Titration in Cell Lysate

Fluorescence titration was performed for the tag polypeptides and the robe polypeptides of Example 1 in a cell lysate.

10 mL of a HeLa cell culture solution containing $1.0 \times 10^6$ cells/mL were dispensed in a centrifugal tube and the cells were centrifuged for 5 minutes at 1000 rpm to obtain a pellet of HeLa cells. The pellet was dispersed in 1 mL HEPES buffer and the dispersion was sonicated for 10 minutes. Subsequently, the dispersion was filtered through a membrane filter to remove undesired materials and thus give a cell lysate. The probe peptide was dissolved in the cell lysate to a concentration of 0.504. To this solution, a tag peptide solution was added dropwise until the solution contained 0.1 to 4.0 equivalents of the tag peptide. The resulting solution was subjected to fluorescence spectroscopy. Fluorescence spectroscopy was performed on Jasco FP-750 spectrofluorometer (Jasco) using a quartz cell having an optical path length of 1 cm.

Figure 9:
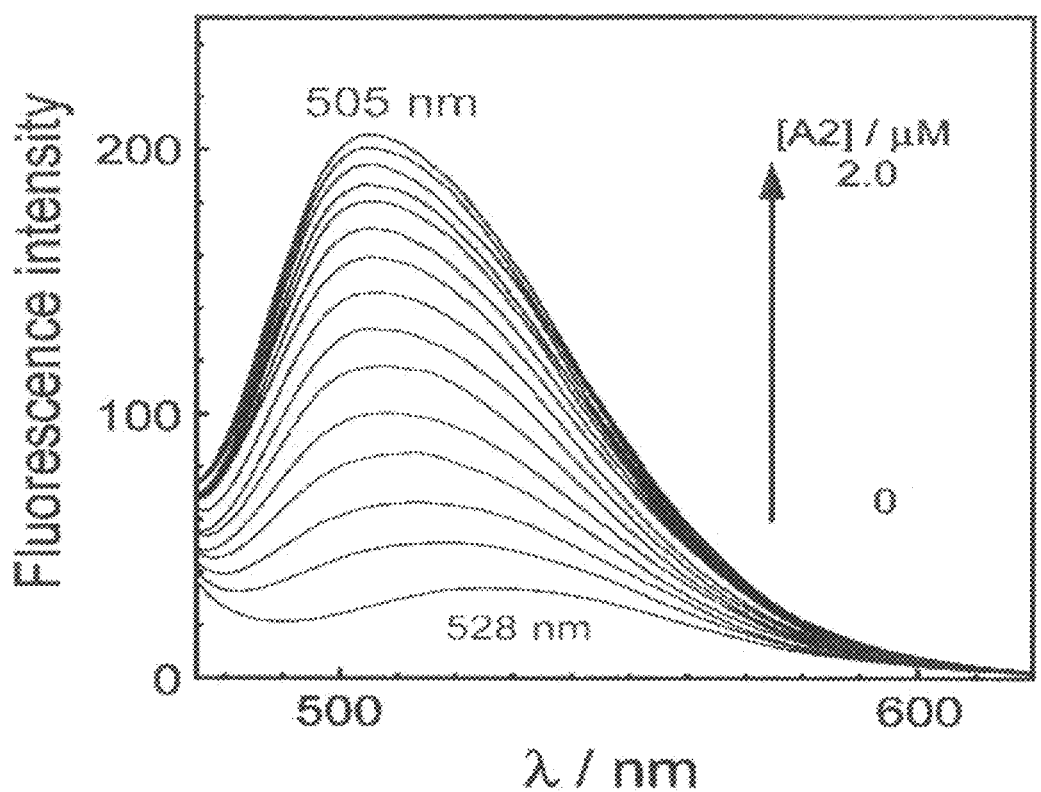
FIG. 9 shows the results of Example 6.

FIG. 9 shows the results of Example 6. In FIG. 9, the horizontal axis represents fluorescence wavelength whereas the vertical axis represents fluorescence intensity As shown in FIG. 9, the probe peptide exhibited substantially the same spectral changes as in HEPES buffer as the tag peptide was added. The slightly high fluorescence intensity at shorter wavelengths is considered to be caused by the fluorescence or scattered light by the components in the cell lysate.

Example 7

Synthesis of Probe Peptide for Crosslink Reaction

In Example 7, a probe peptide for crosslink reaction represented by the following structural formula (14) was synthesized. The probe peptide for crosslink reaction consists of the probe peptide of Example 1 with chloroacetylated glycine added to its N-terminal.

Probe:
(SEQ ID No: 5)
ClAc-{Gly}{Ala-Leu-Lys-Lys-Lys-Leu-Glu}{Ala- (12)
Leu-Lys-Lys-Lys-Dap(NBD)-Glu}{Ala-Leu-Lys-
Lys-Lys-Leu-Ala}

In the structure formula above, ClAc represents a chloroaceryl group.

As in Example 1, the probe peptide was elongated on a 0.05 mmol scale. One glycine residue was then added to the N-terminal as a linker and chloroacetic acid was coupled to introduce the chloroacetyl group. The chloroacetyl group is known to covalently crosslink with the thiol group of a cysteine side chain.

The resin was washed with chloroform and dried in vacuum. To the resulting chloroacetylated peptide-resin, 0.1 mL m-cresol, 0.3 mL thioanisole, 0.04 mL triisopropylsilane and 4 mL trifluoroacetic acid were added and the mixture was stirred at room temperature for 1 hour. Subsequently, the reaction mixture was filtered and the filtrate was concentrated under reduced pressure. To the resulting residue, ice-cooled diethyl ether was added to form a precipitate. The precipitate was centrifuged (at 3000 rpm), washed several times with diethyl ether, and dried in vacuum to obtain crude peptide. The crude peptide was then dissolved in a 10% aqueous acetic acid solution and was purified by HPLC using a C18 reversed-phase semi-preparative column (10×250 mm). The purified product was concentrated under reduced pressure and freeze-dried to give 12.8 mg of the desired probe peptide at 27.8% yield.

HPLC (gradient: A/B=77/23→62/38, 30 min)
Elution time=23.0 min
$[M+H]^+=2662.9$ (Calcd $[M+H]^+=2662.6$)

Example 8

Crosslink Reaction

The probe peptide for crosslink reaction obtained in Example 7 was used to perform a crosslink reaction.

The probe peptide was crosslinked to a tag peptide represented by the following structural formula (8). The tag polypeptide is identical to that used in Example 1.

Tag:
(SEQ ID NO: 1)
{Ala-Leu-Lys-Lys-Glu-Leu-Glu}{Ala-Ala-Lys-Lys- (8)
Glu-Leu-Glu}{Ala-Leu-Lys-Lys-Glu-Leu-Ala}{Gly-
Gly-Cys-Gly-Gly}{Ala-Leu-Glu-Lys-Glu-Leu-Glu}
{Ala-Leu-Glu-Lys-Glu-Ala-Glu}{Ala-Leu-Glu-Lys-
Glu-Leu-Ala}

To a 1.0 μM tag peptide solution (50 mM HEPES buffer (pH 7.2, 10 mM NaCl)), the probe peptide was added to a concentration of 1.0 μM and the reaction was carried out at 25° C. -1 mL samples were collected from the reaction mixture after 1, 5, 10, 15, 20 and 30 minutes. 1 mL of a 10% aqueous acetic acid solution was added to each sample to quench the reaction. The samples were analyzed by HPLC using a C18 reversed-phase analytical column (4.6×250 mm).

The crosslinked product was identified by ESI-TOF MS. The yield of the reaction was calculated from the peak area ratio of HPLC.

HPLC (gradient: A/B=80/20→50/50, 30 min)
Elution time=29.0 min (crosslinked product)
$[M+H]^+=7934.0$ (Calcd $[M+H]^+=7934.2$)

Figure 10:
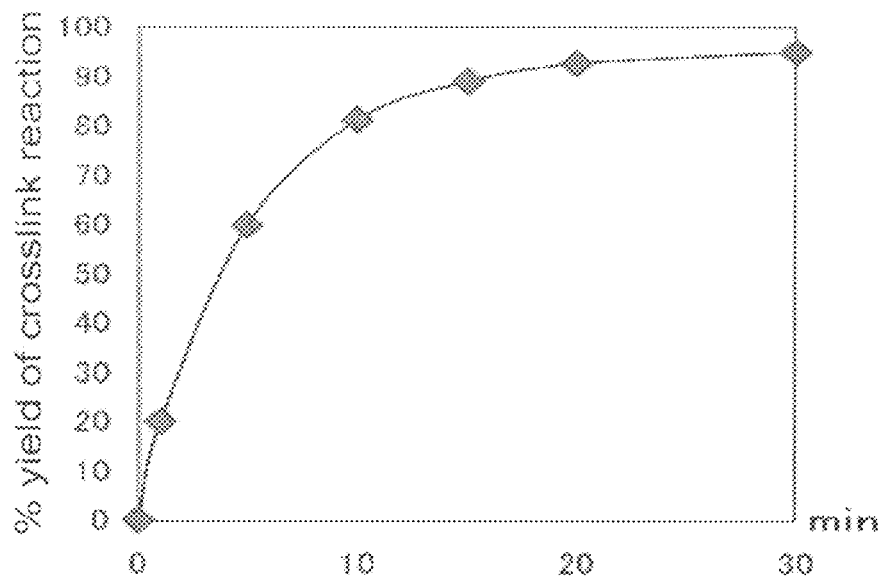
FIG. 10 shows the results of Example 8.

FIG. 10 shows the results of Example 8. In FIG. 10, the horizontal axis represents elapsed time after addition of the probe peptide whereas the vertical axis represents the yield of the crosslink reaction.

FIG. 10 clearly indicates that the tag can form covalent bonds with the probe in a relatively thin solution. The yield of the reaction reached at least 80% 10 minutes after the start of the reaction, indicating quick proceeding of the crosslink reaction.

Example 9

Imaging of Protein Kinase C(PKC) in Cytoplasm of CHO.K1 Cell Through Formation of Tag-Probe Complex

[Observation of NBD]

CHO.K1 cells expressing a fused protein of DsRed and PKC having at its N terminal end a tag polypeptide of sequence (A) as indicated below were prepared using Lipofectamin LTX (Invitrogen).

Sequence (A):
MALKKELEAAKKELEALKKELAGGCGGALEKELEALEKEAEALEKELAGS

GSGSGTDMDYKDDDDKGSMAPFLRIAFNSYELGSLQAEDEANQPFCAVKM

KEALSTERGKTLVQKKPTMYPEWKSTFDAHIYEGRVIQIVLMRAAEEPVS

EVTVGVSVLAERCKKNNGKAEFWLDLQPQAKVLMSVQYFLEDVDCKQSMR

SEDEAKFPTMNRRGAIKQAKLHYIKNHEFIATFFGQPTFCSVCKDFVWGL

NKQGYKCRQCNAAIHKKCIDKIIGRCTGTAANSRDTIFQKERFNIDMPHR

FKVHNYMSPTFCDHCGSLLWGLVKQGLKCEDCGMNVHHKCREKVANLCGI

NQKLLAEALNQVTQRASRRSDSASSEPVGIYQGFEKKTGVAGEDMQDNSG

TYGKIWEGSSKCNINNFIFHKVLGKGSFGKVLLGELKGRGEYFAIKALKK

DVVLIDDDVECTMVEKRVLTLAAENPFLTHLICTFQTKDHLFFVMEFLNG

GDLMYHIQDKGRFELYRATFYAAEMCGLQFLHSKGIIYRDLKLDNVLLDR

DGHIKIADFGMCKENIFGESRASTFCGTPDYIAPEILQGLKYTFSVDWWS

FGVLLYELIGQSPFHGDDEDELFESIRVDTPHYPRWITKESKDILEKLFE

REPTKRLGVTGNIKIHPFFKTINWTLLEKRRLEPPFRPKVKSPRDYSNFD

QEFLNEKARLSYSDKNLIDSMDQSAFAGFSFVNPKFEHLLED

Subsequently, a permeabilization buffer (20 mM Hepes, pH 7.4, 140 mM KCl, 50 μg/mL saponin, 5 mM oxalic acid) was added to the thus-prepared CHO.K1 cells. After left to stand on ice for 10 min, the cells were washed with PBS, followed by incubating on ice for 20 min in PBS. Thereafter, the cells were incubated in PBS at room temperature for 2 min and then 37° C. for 2 min. Further, the cells were incubated at 37° C. for 30 min in a conditioned medium (Ham's F12) to which a probe indicated by sequence (B) (probe concentration: 1 μM (Final conc.)) had been added.

Sequence (B):
ClCH$_2$CONH-G ALKKKLE ALKKKXE ALKKKLA-CONH$_2$

The medium was changed to a DMEM with no phenol red, and then, the cells were observed by a fluorescence microscope (IX81 (Olympus), objective lens: 20 times) at predetermined emission wavelength (490 nm to 510 nm).

Separately, before treated with the permeabilization buffer, the above-prepared CHO.K1 cells were treated for 10 min with 10 mM DMSO containing PDBu (phorbol 12,13 dibutyrate; final concentration: 10 μM). The cells were observed by the fluorescence microscope similar to the above. The results are shown in FIG. 11.

Figure 11:
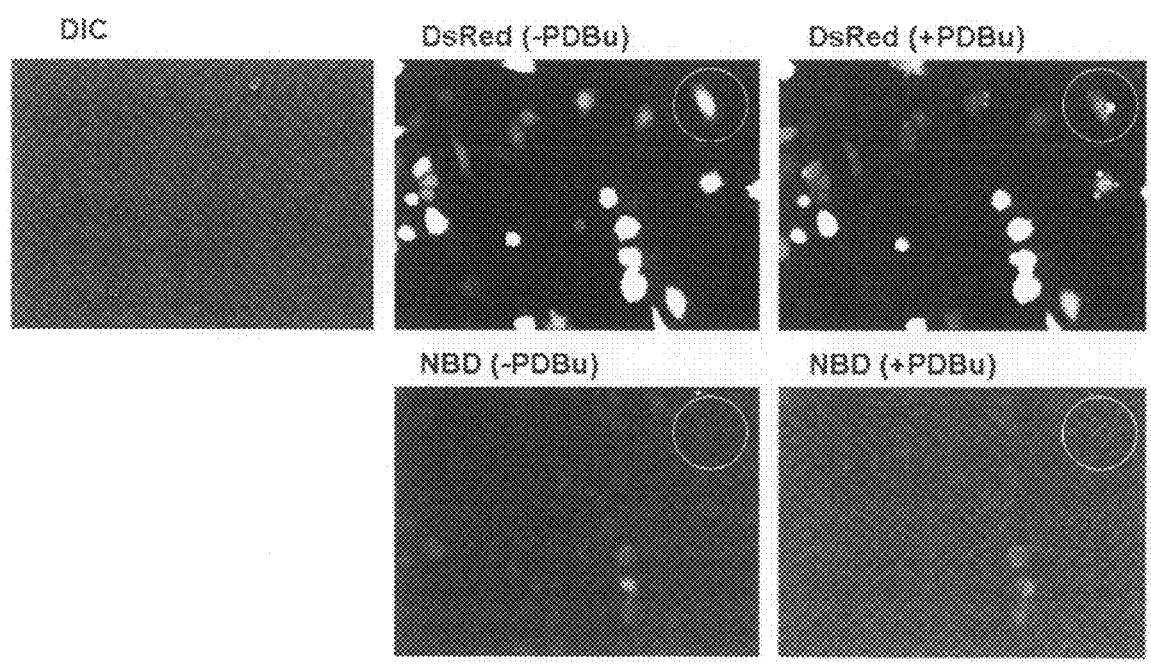
FIG. 11 shows the results of Example 9.

As shown in two lower photographs of FIG. 11, an increase in fluorescence intensity at around 510 nm was observed which was derived from NBD. Also, the fluorescence derived from NBD was observed throughout the cytoplasm of each cell which had not been treated with PDBu, in contrast, the fluorescence derived from NBD was locally observed in the cytoplasm of each cell which had been treated with PDBu.

[Localization of PKC in Cytoplasm]

Separately, the above-mentioned CHO.K1 cells expressing a fused protein of DsRed and PKC having at its N terminal end a tag polypeptide indicated by sequence (A), which had been treated with or without PDBu, were observed for the fluorescence from DsRed. The following was used as a control; a group which was not treated with PDBu, and CHO.K1 cells to which only DIC was introduced (note that DIC is a vector used for introducing into cells the above-mentioned fused protein of DsRed and PKC having at its N terminal end a tag polypeptide indicated by sequence (A). The cells were observed as mentioned above at predetermined wavelength (515 nm to 560 nm). The results are shown in FIG. 11.

As a result, in the CHO.K1 cells which had not been treated with PDBu, the fluorescence derived from DsRed was observed throughout each cell. In contrast, in the CHO.K1 cells which had been treated with PDBu, the fluorescence derived from DsRed was locally observed in their cytoplasm. The aspect in which the fluorescence derived from DsRed was localized was similar to that in which the fluorescence derived from NBD was localized in

[Observation of NBD].

These indicate that an increase in fluorescence intensity observed in [Observation of NBD] is derived from the formation of a tag-probe complex in the cells.

The method for detecting a target substance in accordance with the present invention can not only visualize the expression of a target substance at any time point while reducing influences on the functions of the target substance, but it can also use fluorescent dyes having various excitation/emission wavelengths and achieve easy staining process. Therefore, the method is suitable for use in the study of the structure and function of various proteins. Accordingly, the method of the present invention for detecting a target substance should find applications in the study of biological mechanisms and diseases. Furthermore, the tag, the DNA, the vector, the probe and the detection kit for use in the above-described detection method are suitably used as reagents and kits in studies such as those described above.

---

What is claimed is:

1. A method for detecting a target substance, comprising:
   bringing into contact with each other (a) a tag comprising a polypeptide forming an α-helix structure, the tag bound to the target substance, and (b) a probe comprising a compound bound to a fluorescent dye; and
   measuring the fluorescence emitted by the fluorescent dye,
   wherein a binding of the α-helix structure of the tag to the compound of the probe induces a spectral change in the fluorescence emitted by the fluorescent dye,
   wherein the compound of the probe comprises a polypeptide forming an α-helix structure, and
   wherein the polypeptide of the tag comprises a sequence represented by the following structural formula (2) and the polypeptide of the probe comprises a sequence represented by the following structural formula (3):

Tag:
$\{X_1-\epsilon_1-\alpha-X_4-\beta-\gamma-X_7\}\{X_1-\epsilon_2-\alpha-X_4-\beta-\gamma-X_7\}\{X_1-\epsilon_3-\alpha-X_4-\beta-\gamma-X_7\}\{X_M\}\{X_1-\gamma-\beta-X_4-\beta-\epsilon_3-X_7\}\{X_1-\gamma-\beta-X_4-\beta-\epsilon_2-X_7\}\{X_1-\gamma-\beta-X_4-\beta-\epsilon_1-X_7\}$ (2)

Probe:
$\{X_1-\gamma-\alpha-X_4-\alpha-\sigma_1-X_7\}\{X_1-\gamma-\alpha-X_4-\alpha-\sigma_2-X_7\}\{X_1-\gamma-\alpha-X_4-\alpha-\sigma_3-X_7\}$ (3)

wherein
   α is an acidic amino acid or a basic amino acid;
   β is a basic amino acid when α is an acidic amino acid, and is an acidic amino acid when α is a basic amino acid;
   γ is a hydrophobic amino acid;
   at least one of $\sigma_1$ to $\sigma_3$ is a molecule bound to a fluorescent dye and the rest of $\sigma_1$ to $\sigma_3$ are each a hydrophobic amino acid;
   $\epsilon_1$ is each independently one of glycine, alanine, valine, serine, threonine and asparagine when $\sigma_1$ is the fluorescent dye-bound molecule, and is each independently a hydrophobic amino acid when $\sigma_2$ is a hydrophobic amino acid;
   $\epsilon_2$ is each independently one of glycine, alanine, valine, serine, threonine and asparagine when $\sigma_2$ is the fluorescent dye-bound molecule, and is each independently a hydrophobic amino acid when $\sigma_2$ is a hydrophobic amino acid;
   $\epsilon_3$ is each independently one of glycine, alanine, valine, serine, threonine and asparagine when $\sigma_3$ is the fluorescent dye-bound molecule, and is each independently a hydrophobic amino acid when $\sigma_3$ is a hydrophobic amino acid;
   $X_1$, $X_4$ and $X_7$ are each any amino acid; and
   $X_M$ is a linker peptide comprising M amino acids where M represents a number.

2. The method according to claim 1, wherein the binding of the α-helix structure of the tag to the compound of the probe comprises hydrophobic interaction.

3. The method according to claim 2, wherein the binding of the α-helix structure of the tag to the compound of the probe comprises electrostatic interaction.

4. The method according to claim 3, wherein at least one α-helix structure of the tag and at least one α-helix structure of the probe are associated with each other in at least one of parallel orientation and antiparallel orientation, forming a tag-probe complex with the hydrophobic surface of each α-helix facing inward.

5. The method according to claim 1, wherein the polypeptide of the tag comprises a sequence represented by the following structural formula (4) and the polypeptide of the probe comprises a sequence represented by the following structural formula (5):

Tag:
$\{Ala-\gamma-\alpha-Lys-\beta-\gamma-Glu\}\{Ala-\epsilon_2-\alpha-Lys-\beta-\gamma-Glu\}$ (4)

$\{Ala-\gamma-\alpha-Lys-\beta-\gamma-Ala\}\{X_M\}\{Ala-\gamma-\beta-Lys-\beta-\gamma-Glu\}$ $\{Ala-\gamma-\beta-Lys-\beta-\epsilon_2-Glu\}\{Ala-\gamma-\beta-Lys-\beta-\gamma-Ala\}$ Probe:
$\{Ala-\gamma-\alpha-Lys-\alpha-\gamma-Glu\}\{Ala-\gamma-\alpha-Lys-\alpha-\sigma_2-Glu\}$ (5)

$\{Ala-\gamma-\alpha-Lys-\alpha-\gamma-Ala\}$ wherein
   α is an acidic amino acid or a basic amino acid;
   β is a basic amino acid when α is an acidic amino acid, and is an acidic amino acid when α is a basic amino acid;
   γ is a hydrophobic amino acid;
   $\sigma_2$ is a molecule bound to a fluorescent dye;
   $\epsilon_2$ is each independently one of glycine, alanine, valine, serine, threonine and asparagine; and
   $X_M$ is a linker peptide comprising M amino acids where M represents a number.

6. The method according to claim 1, wherein the polypeptide of the tag comprises a sequence represented by the following structural formula (6) and the polypeptide of the probe comprises a sequence represented by the following structural formula (7):

Tag:
$\{Ala-Leu-Lys-Lys-Glu-Leu-Glu\}\{Ala-\epsilon_2-Lys-Lys-Glu-Leu-Glu\}\{Ala-Leu-Lys-Lys-Glu-Leu-Ala\}\{X_M\}$ (6)

$\{Ala-Leu-Glu-Lys-Glu-Leu-Glu\}\{Ala-Leu-Glu-Lys-Glu-\epsilon_2-Glu\}\{Ala-Leu-Glu-Lys-Glu-Leu-Ala\}$ Probe:
$\{Ala-Leu-Lys-Lys-Lys-Leu-Glu\}\{Ala-Leu-Lys-Lys-Lys-\sigma_2-Glu\}\{Ala-Leu-Lys-Lys-Lys-Leu-Ala\}$ (7)

wherein
   $\sigma_2$ is a molecule bound to a fluorescent dye;
   $\epsilon_2$ is each independently one of glycine, alanine, valine, serine, threonine and asparagine; and
   $X_M$ is a linker peptide comprising M amino acids where M represents a number.

7. The method according to claim 1, wherein the fluorescent dye is any of NBD (4-nitrobenzo-2-oxa-1,3-diazole), Dns (dansyl; 1-dimethylaminonaphthalene-5-sulfonyl), DAN (6-dimethylamino-2-naphthoyl), Ant (anthraniloyl), Mant (N-methylanthraniloyl), DMAP (4-dimethylaminophthalimide), DMAN (6-dimethylamino-2,3-naphthalimide), 3-dimethylaminobenzonitrile, ANS (1-anilinonaphthalene-8-sulfonic acid), MANS(N-methyl-2-anilinonaphthalene-6-sulfonic acid), TNS (2-p-toluidinylnaphthalene-6-sulfonic acid), dimethylaminophenoxazone, Nile Red, DAPDXYL SULFONYL (Registered trademark), indocyanine green, 7-hydroxycoumarin-3-carboxylic acid, 7-diethylaminocoumarin-3-carboxylic acid, fluorescein, 2,7-dichrolofluorescein, TAMRA (tetramethyl rhodamin), Cy3, Cy5, Cy7, coumarins, anthracene and pyrene.

* * * * *